US009637746B2

(12) United States Patent
Klein-Marcuschamer

(10) Patent No.: US 9,637,746 B2
(45) Date of Patent: May 2, 2017

(54) METHODS FOR CONTROL OF FLUX IN METABOLIC PATHWAYS

(75) Inventor: Daniel Klein-Marcuschamer, San Francisco, CA (US)

(73) Assignee: GreenLight Biosciences, Inc., Medford, MA (US)

(*) Notice: Subject to any disclaimer, the term of this patent is extended or adjusted under 35 U.S.C. 154(b) by 819 days.

(21) Appl. No.: 13/132,721

(22) PCT Filed: Dec. 14, 2009

(86) PCT No.: PCT/US2009/067841
§ 371 (c)(1),
(2), (4) Date: Jul. 12, 2011

(87) PCT Pub. No.: WO2010/077806
PCT Pub. Date: Jul. 8, 2010

(65) Prior Publication Data
US 2011/0269198 A1    Nov. 3, 2011

Related U.S. Application Data

(60) Provisional application No. 61/201,783, filed on Dec. 15, 2008.

(51) Int. Cl.
C12N 15/52      (2006.01)
C12N 9/22       (2006.01)
C12P 7/42       (2006.01)

(52) U.S. Cl.
CPC ............... *C12N 15/52* (2013.01); *C12N 9/22* (2013.01); *C12P 7/42* (2013.01); *Y02P 20/52* (2015.11)

(58) Field of Classification Search
CPC . C12N 9/22; C12N 9/48; C12N 15/52; C12N 1/18; C12P 7/42
See application file for complete search history.

(56) References Cited

U.S. PATENT DOCUMENTS

| | | |
|---|---|---|
| 3,684,652 A | 8/1972 | Nakayama et al. |
| 3,950,357 A | 4/1976 | Kahan et al. |
| RE28,886 E | 6/1976 | Nakayama et al. |
| 4,006,060 A | 2/1977 | Kahan et al. |
| 4,194,047 A | 3/1980 | Christensen et al. |
| 4,248,966 A | 2/1981 | Demain et al. |
| 4,266,034 A | 5/1981 | Patel |
| 4,270,537 A | 6/1981 | Romaine |
| 4,292,436 A | 9/1981 | Liu et al. |
| 4,329,481 A | 5/1982 | Liu et al. |
| 4,374,772 A | 2/1983 | Hazen et al. |
| 4,438,201 A | 3/1984 | Kubo et al. |
| 4,458,066 A | 7/1984 | Caruthers et al. |
| 4,460,689 A | 7/1984 | Foor et al. |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 4,946,783 A | 8/1990 | Beckwith et al. |
| 4,950,603 A | 8/1990 | Ingolia et al. |
| 5,001,055 A | 3/1991 | Imahori et al. |
| 5,015,235 A | 5/1991 | Crossman |
| 5,064,413 A | 11/1991 | McKinnon et al. |
| 5,070,020 A | 12/1991 | Ingolia et al. |
| 5,141,496 A | 8/1992 | Dalto et al. |
| 5,190,521 A | 3/1993 | Hubbard et al. |
| 5,312,335 A | 5/1994 | McKinnon et al. |
| 5,319,122 A | 6/1994 | Friedman |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,436,131 A | 7/1995 | Condra et al. |
| 5,466,220 A | 11/1995 | Brenneman |
| 5,480,381 A | 1/1996 | Weston |
| 5,503,627 A | 4/1996 | McKinnon et al. |

(Continued)

FOREIGN PATENT DOCUMENTS

| | | |
|---|---|---|
| CN | 1329506 C | 8/2007 |
| EP | 0377295 A1 | 7/1990 |
| EP | 0444775 A1 | 9/1991 |
| EP | 0553821 A1 | 8/1993 |
| EP | 1 433 856 A1 | 6/2004 |
| EP | 1502956 A1 | 2/2005 |
| EP | 1939210 A1 | 7/2008 |
| EP | 2204453 A1 | 7/2010 |
| GB | 2 018 822 A | 10/1979 |
| JP | S61-260895 A | 11/1986 |

(Continued)

OTHER PUBLICATIONS

Krell, T., et al., 1997, "Crystallization and preliminary X-ray crystallographic analysis of shikimate kinase from Erwinia chrysanthemi", Acta Crystallographica, Sect. D, vol. 53, pp. 612-614.*

Romanowski, M.J., et al., 2002, "Crystal structure of the Escherichia coli shikimate kinase I (AroK) that confers sensitivity to mecillinam", Proteins, vol. 47, pp. 558-562.*

Kim, H.B., et al., 2004, "Metabolic flux analysis for calcium dependent antibiotic (CDA) production in Streptomyces coelicolor", Metabolic Engineering, vol. 6, pp. 313-325.*

(Continued)

Primary Examiner — Nashaat Nashed
Assistant Examiner — William W Moore
(74) Attorney, Agent, or Firm — Wolf, Greenfield & Sacks, P.C.

(57) ABSTRACT

The invention pertains to a method for preparing cells that can be used as biocatalysts by inducing in them a growth-decoupled state, in which interferase inhibits the expression of genes except the ones that code for the pathway enzymes of interest. mRNAs that code for interferase-resistant products are overexpressed in the background of a metabolically-frozen cell. Enzymes that compete for a substrate or product of the pathway of interest may be altered such that the enzyme is sensitive to a site-specific protease, which protease is inducible in the host cell.

14 Claims, 6 Drawing Sheets

(56) References Cited

U.S. PATENT DOCUMENTS

| | | | |
|---|---|---|---|
| 5,520,639 A | 5/1996 | Peterson et al. | |
| 5,527,288 A | 6/1996 | Gross et al. | |
| 5,569,189 A | 10/1996 | Parsons | |
| 5,593,856 A | 1/1997 | Choi et al. | |
| 5,599,302 A | 2/1997 | Lilley et al. | |
| 5,649,912 A | 7/1997 | Peterson | |
| 5,665,566 A | 9/1997 | Lavalle | |
| 5,672,497 A | 9/1997 | Cox et al. | |
| 5,704,911 A | 1/1998 | Parsons | |
| 5,871,922 A | 2/1999 | Salmond et al. | |
| 5,893,397 A | 4/1999 | Peterson et al. | |
| 5,993,412 A | 11/1999 | Deily et al. | |
| 6,168,931 B1 | 1/2001 | Swartz et al. | |
| 6,387,667 B1 | 5/2002 | Maruyama et al. | |
| 6,440,688 B1 | 8/2002 | Bruce et al. | |
| 6,472,169 B1 | 10/2002 | Frost et al. | |
| 6,531,299 B1 | 3/2003 | Khosla et al. | |
| 6,613,552 B1* | 9/2003 | Frost | C12N 9/0006 435/132 |
| 6,746,859 B1 | 6/2004 | LaVallie | |
| 6,921,659 B2 | 7/2005 | Joly | |
| 6,994,986 B2 | 2/2006 | Swartz et al. | |
| 7,041,479 B2 | 5/2006 | Swartz et al. | |
| 7,223,390 B2 | 5/2007 | Brown | |
| 7,226,767 B2 | 6/2007 | Maruyama et al. | |
| 7,312,049 B2 | 12/2007 | Calhoun et al. | |
| 7,338,789 B2 | 3/2008 | Swartz et al. | |
| 7,341,852 B2 | 3/2008 | Voloshin et al. | |
| 7,351,563 B2 | 4/2008 | Swartz et al. | |
| 8,859,247 B2 | 10/2014 | Koltermann et al. | |
| 8,916,358 B2 | 12/2014 | Swartz | |
| 8,956,833 B2 | 2/2015 | Swartz | |
| 2002/0058303 A1 | 5/2002 | Swartz et al. | |
| 2002/0127633 A1 | 9/2002 | Dilley et al. | |
| 2002/0160459 A1* | 10/2002 | Berry | C12N 9/1096 435/72 |
| 2003/0022178 A1 | 1/2003 | Schneewind et al. | |
| 2003/0040086 A1* | 2/2003 | Dodge | C12N 15/52 435/126 |
| 2003/0113778 A1 | 6/2003 | Schulte et al. | |
| 2004/0002103 A1 | 1/2004 | Short | |
| 2004/0038250 A1 | 2/2004 | Nunez et al. | |
| 2004/0091976 A1* | 5/2004 | Deng | C12P 19/26 435/84 |
| 2004/0209321 A1 | 10/2004 | Swartz et al. | |
| 2005/0054044 A1 | 3/2005 | Swartz et al. | |
| 2005/0239174 A1* | 10/2005 | Bao | C12P 19/02 435/105 |
| 2006/0234358 A1* | 10/2006 | Anderlei | C12P 13/22 435/108 |
| 2006/0281148 A1 | 12/2006 | Swartz et al. | |
| 2007/0111283 A1 | 5/2007 | Cannon et al. | |
| 2007/0154983 A1 | 7/2007 | Calhoun et al. | |
| 2007/0161092 A1* | 7/2007 | Townsend | C12P 17/188 435/117 |
| 2007/0202198 A1 | 8/2007 | Purcell | |
| 2008/0131925 A1 | 6/2008 | Berk et al. | |
| 2009/0053779 A1* | 2/2009 | Lee | C12N 9/1014 435/115 |
| 2009/0124012 A1* | 5/2009 | Nikolsky | C12N 9/22 435/455 |
| 2009/0155867 A1* | 6/2009 | Soucaille | C12P 7/42 435/135 |
| 2009/0275096 A1 | 11/2009 | Burgard et al. | |
| 2009/0275097 A1* | 11/2009 | Sun | C12N 9/0006 435/160 |
| 2009/0312539 A1 | 12/2009 | Gnanaprakasam et al. | |
| 2009/0325245 A1* | 12/2009 | Soucaille | C12P 13/001 435/128 |
| 2010/0120105 A1* | 5/2010 | Anthony | C12N 9/0006 435/157 |
| 2010/0143997 A1* | 6/2010 | Buelter | C12N 9/0006 435/160 |
| 2010/0291653 A1 | 11/2010 | Ness et al. | |
| 2011/0008867 A1 | 1/2011 | Zarur et al. | |
| 2011/0099670 A1 | 4/2011 | Koops et al. | |
| 2011/0124069 A1* | 5/2011 | Mampel | C12P 7/18 435/158 |
| 2011/0262946 A1 | 10/2011 | Roy et al. | |
| 2011/0275116 A1 | 11/2011 | Swartz | |
| 2011/0312052 A1 | 12/2011 | Koltermann et al. | |
| 2012/0052547 A1 | 3/2012 | Swartz | |
| 2012/0070870 A1 | 3/2012 | Way et al. | |
| 2013/0065878 A1 | 3/2013 | Blake et al. | |
| 2014/0193869 A1 | 7/2014 | Blake et al. | |
| 2015/0037868 A1 | 2/2015 | Blake et al. | |
| 2015/0064751 A1 | 3/2015 | Swartz | |
| 2015/0191753 A1 | 7/2015 | Swartz | |
| 2016/0115558 A1 | 4/2016 | Swartz | |

FOREIGN PATENT DOCUMENTS

| | | |
|---|---|---|
| JP | S63-7788 A | 1/1988 |
| JP | H01-2287473 A | 9/1989 |
| JP | H07-298893 A | 11/1995 |
| JP | H08-502176 A | 3/1996 |
| JP | H08-196284 A | 8/1996 |
| JP | 2002-535008 A | 10/2002 |
| JP | 2007-534338 A | 11/2007 |
| JP | 2009-531050 A | 9/2009 |
| WO | WO 97/13537 A1 | 4/1997 |
| WO | WO 97/37705 A1 | 10/1997 |
| WO | WO 98/07690 A1 | 2/1998 |
| WO | WO 99/34850 A1 | 7/1999 |
| WO | WO 00/39288 A1 | 7/2000 |
| WO | WO 00/44923 A1 | 8/2000 |
| WO | WO 00/55353 A1 | 9/2000 |
| WO | WO 03/038117 A2 | 5/2003 |
| WO | WO 2005/030949 A1 | 4/2005 |
| WO | WO 2005/098048 A1 | 10/2005 |
| WO | WO 2006/001382 A1 | 1/2006 |
| WO | WO 2006/090385 A2 | 8/2006 |
| WO | WO 2007/053655 A2 | 5/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | WO 2011/017560 A1 | 2/2011 |
| WO | WO 2011/072287 A2 | 6/2011 |
| WO | WO 2011/140516 A2 | 11/2011 |
| WO | WO 2012/030980 A1 | 3/2012 |
| WO | WO 2012/135902 A1 | 10/2012 |
| WO | WO 2014/197655 A1 | 12/2014 |

OTHER PUBLICATIONS

Ding, L., et al., 2007, "Functional analysis of the essential bifunctional tobacco enzyme 3-dehydroquinate dehydratase/shikimate dehydrogenase in transgenic tobacco plants", Journal of Experimental Botany, vol. 58, No. 8, pp. 2053-2067.*

Yamaguchi, Y., et al., 2009, "MqsR, a crucial regulator for quorum sensing and biofilm formation, is a GCU-specific mRNA interferase in *Escherichia coli*", The Journal of Biological Chemistry, vol. 284, No. 42, pp. 28746-28753.*

Horak, J., et al., 2002, "Two distinct proteolytic systems responsible for glucose-induced degradation of fructose-1,6-bisphosphatase and the Gal2p transporter in the yeast *Saccharomyces cerevisiae* share the same protein components of the glucose signaling pathway", The Journal of Biological Chemistry, vol. 277, No. 10, pp. 8248-8254.*

Li, R:, et al., 2006, "Rational strain improvement for enhanced clavulanic acid production by genetic engineering of the glycolytic pathway in Streptomyces clavuligerus", Metabolic Engineering, vol. 8, pp. 240-252.*

(56) References Cited

OTHER PUBLICATIONS

Brady, C.L., et al., 2010, "Transfer of Pantoea citrea, Pantoea punctata and Pantoea terrea to the genus *Tatumella* emend. as Tatumella citrea comb. nov., Tatumella punctata comb. nov. and Tatumella terrea comb. nov. and description of *Tatumella morbirosei* sp. nov.", Internat'l Journal of Systematic and Evolutionary Microbiology, vol. 60, 484-494.*
Invitation to Pay Additional Fees for PCT/US2011/035639 mailed Sep. 12, 2011.
International Search Report and Written Opinion for PCT/US2011/035639 mailed Nov. 18, 2011.
International Search Report and Written Opinion for PCT/US2009/067841mailed Mar. 22, 2010.
International Preliminary Report on Patentability for PCT/US2009/067841 mailed Jun. 21, 2011.
International Search Report and Written Opinion for PCT/US2009/006704 mailed Mar. 3, 2010.
International Preliminary Report on Patentability for PCT/US2009/006704 mailed Jul. 7, 2011.
[No Author Listed] Biolistic® Particle Delivery System Bibliography. Bio-Rad Technical Bulletin #1687. Bio-Rad Laboratories. 12 pages.
[No Author Listed] Biapenem. Drugs Fut. 1994;19(7):631-637.
Adams et al., Hindered dialkylamino nucleoside phosphite reagents in the synthesis of two DNA 51-mers. J Am Chem Soc. 1983;105(3):661-3.
Alber et al., Malonyl-coenzyme A reductase in the modified 3-hydroxypropionate cycle for autotrophic carbon fixation in archaeal Metallosphaera and *Sulfolobus* spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Alper et al., Tuning genetic control through promoter engineering. Proc Natl Acad Sci U S A. Sep. 6, 2005;102(36):12678-83. Epub Aug. 25, 2005.
Alves-Pereira et al., CDP-alcohol hydrolase, a very efficient activity of the 5'-nucleotidase/udp-sugar hydrolase encoded by the usha gene of yersinia intermedia and *escherichia coli*. J Bacteriol. Sep. 15, 2008;190(18):6153-61. Published ahead of print Jul. 18, 2008 , doi:10.1128/JB.00658-08.
Anthony et al., Optimization of the mevalonate-based isoprenoid biosynthetic pathway in *Escherichia coli* for production of the anti-malarial drug precursor amorpha-4,11-diene. Metab Eng. Jan. 2009;11(1):13-9. Epub Aug. 12, 2008.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.
Baum et al., beta-Galactosidase containing a human immunodeficiency virus protease cleavage site is cleaved and inactivated by human immunodeficiency virus protease. Proc Natl Acad Sci U S A. Dec. 1990;87(24):10023-7.
Beaucage et al., Deoxynucleoside phosphoramidites—A new class of key intermediates for deoxypolynucleotide synthesis. Tetra Lett. 1981;22(20):1859-62.
Belousov et al., Sequence-specific targeting and covalent modification of human genomic DNA. Nucleic Acids Res. Sep. 1, 1997;25(17):3440-4.
Benton et al., Screening lambdagt recombinant clones by hybridization to single plaques in situ. Science. Apr. 8, 1977;196(4286):180-2.
Berge et al., Pharmaceutical salts. J Pharmaceut Sci. Jan. 1997;66(1):1-19.
Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry. Jun. 28, 1994;33(25):7886-96.
Bodner et al., Non-heme iron oxygenases generate natural structural diversity in carbapenem antibiotics. J Am Chem Soc. Jan. 13, 2010;132(1):12-3.
Boiteux et al., Design of glycolysis. Philos Trans R Soc Lond B Biol Sci. Jun. 26, 1981;293(1063):5-22.
Bongaerts et al., Metabolic engineering for microbial production of aromatic amino acids and derived compounds. Metab Eng. Oct. 2001;3(4):289-300.
Boyer et al., Cell-free synthesis and maturation of [FeFe] hydrogenases. Biotechnol Bioeng. Jan. 1, 2008;99(1):59-67.
Bradley, Star role for bacteria in controlling flu pandemic? Nat Rev Drug Discov. Dec. 2005;4(12):945-6.
Brown et al., Chemical synthesis and cloning of a tyrosine tRNA gene. Methods Enzymol. 1979;68:109-51.
Buist et al., Different subcellular locations of secretome components of Gram-positive bacteria. Microbiology. Oct. 2006;152(Pt 10):2867-74.
Calhoun et al., An economical method for cell-free protein synthesis using glucose and nucleoside monophosphates. Biotechnol Prog. Jul.-Aug. 2005;21(4):1146-53.
Calhoun et al., Energizing cell-free protein synthesis with glucose metabolism. Biotechnol Bioeng. Jun. 5, 2005;90(5):606-13.
Calhoun et al., Energy systems for ATP regeneration in cell-free protein synthesis reactions. Methods in Molecular Biology. In vitro transcription and translation protocols. 375(2):3-17.
Calhoun et al., Total amino acid stabilization during cell-free protein synthesis reactions. J Biotechnol. May 17, 2006;123(2):193-203. Epub Jan. 26, 2006.
Campbell et al., The CTP:phosphocholine cytidylyltransferase encoded by the licC gene of *Streptococcus pneumoniae*: cloning, expression, purification, and characterization. Biochim Biophys Acta. Dec. 30, 2001;1534(2-3):85-95.
Chandran et al., Phosphoenolpyruvate availability and the biosynthesis of shikimic acid. Biotechnol Prog. May-Jun. 2003;19(3):808-14.
Chang et al., YPA: an integrated repository of promoter features in *Saccharomyces cerevisiae*. Nucleic Acids Res. Jan. 2011;39(Database issue):D647-52. Epub Nov. 2, 2010.
Chen et al., A modified osmotic shock for periplasmic release of a recombinant creatinase from *Escherichia coli*. Biochem Eng J. 2004;19:211-5.
Chen et al., Crystal structures of penicillin-binding protein 6 from *Escherichia coli*. J Am Chem Soc. Oct. 14, 2009;131(40):14345-54.
Chen et al., High-level accumulation of a recombinant antibody fragment in the periplasm of *Escherichia coli* requires a triple-mutant (degP prc spr) host strain. Biotechnol Bioeng. Mar. 5, 2004;85(5):463-74.
Chiu et al., Site-directed, Ligase-Independent Mutagenesis (SLIM): a single-tube methodology approaching 100% efficiency in 4 h. Nucleic Acids Res. Dec. 7, 2004;32(21):e174.
Chong et al., Single-column purification of free recombinant proteins using a self-cleavable affinity tag derived from a protein splicing element. Gene. Jun. 19, 1997;192(2):271-81.
Choubey et al., Molecular characterization and localization of Plasmodium falciparum choline kinase. Biochim Biophys Acta. Jul. 2006;1760(7):1027-38.
Coulthurst et al., Regulation and biosynthesis of carbapenem antibiotics in bacteria. Nat Rev Microbiol. Apr. 2005;3(4):295-306. Erratum included.
Dahiyat et al., De novo protein design: fully automated sequence selection. Science. Oct. 3, 1997;278(5335):82-7.
Dahl et al., Isolation and characterization of Chinese hamster ovary cells defective in the intracellular metabolism of low density lipoprotein-derived cholesterol. J Biol Chem. Mar. 5, 1992;267(7):4889-96.
Dani et al., Isolation and characterization of a thylakoid membrane module showing partial light and dark reactions. Biochim Biophys Acta. May 15, 2005;1669(1):43-52.
Daniell et al., Transformation of the cyanobacterium Anacystis nidulans 6301 with the *Escherichia coli* plasmid pBR322. Proc Natl Acad Sci U S A. Apr. 1986;83(8):2546-50.

(56) References Cited

OTHER PUBLICATIONS

Datsenko et al., One-step inactivation of chromosomal genes in *Escherichia coli* K-12 using PCR products. Proc Natl Acad Sci U S A. Jun. 6, 2000;97(12):6640-5.
De Boer et al., Protein targeting towards the thylakoid lumen of chloroplasts: proper localization of fusion proteins is only observed in vivo. EMBO J. Oct. 1991;10(10):2765-72.
De Mey et al., Construction and model-based analysis of a promoter library for *E. coli*: an indispensable tool for metabolic engineering. BMC Biotechnol. Jun. 18, 2007;7:34.
Dietrich et al., A novel semi-biosynthetic route for artemisinin production using engineered substrate-promiscuous P450(BM3). ACS Chem Biol. Apr. 17, 2009;4(4):261-7.
Dingwall et al., The nucleoplasmin nuclear location sequence is larger and more complex than that of SV-40 large T antigen. J Cell Biol. Sep. 1988;107(3):841-9.
Draper et al., Ti plasmid homologous sequences present in tissues from agrobacterium plasmid-transformed petunia protoplasts. Plant Cell Physiol. 1982;23(3):451-8.
Elander, Industrial production of beta-lactam antibiotics. Appl Microbiol Biotechnol. Jun. 2003;61(5-6):385-92. Epub Apr. 3, 2003.
Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.
Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.
Evans et al., The asymmetric synthesis of β-lactam antibiotics—IV. A formal synthesis of thienamycin. Tetra Lett. 1986;27(41):4961-4.
Flores et al., Pathway engineering for the production of aromatic compounds in *Escherichia coli*. Nat Biotechnol. May 1996;14(5):620-3.
Freeman et al., Four enzymes define the incorporation of coenzyme A in thienamycin biosynthesis. Proc Natl Acad Sci U S A. Aug. 12, 2008;105(32):11128-33. Epub Aug. 4, 2008.
Freeman et al., A comparison of methods for plasmid delivery into plant protoplasts. Plant Cell Physiol. 1984;25(8):1353-65.
Frenkel et al., 7,12-dimethylbenz[a]anthracene induces oxidative DNA modification in vivo. Free Radic Biol Med. Sep. 1995;19(3):373-80.
Friesen et al., Purification and Kinetic Characterization of CPT:Phosphocholine Cytidylyltransferase from *Saccharomyces cerevisiae*. Protein Expression and Purification. Feb. 2001;21(1):141-8.
Fromm et al., Stable transformation of maize after gene transfer by electroporation. Nature. Feb. 27-Mar. 5, 1986;319(6056):791-3.
Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.
Gaspar et al., High yields of 2,3-butanediol and mannitol in Lactococcus lactis through engineering of Nad+ cofactor recycling. Appl Environ Microbiol. Oct. 2011;77(19):6826-35. Epub Aug. 12, 2011. Supplemental material included.
Ger et al., a single Ser-180 mutation desensitizes feedback inhibition of the phenylalanine-sensitive3-deoxy-D-arabino-heptulosonate 7-phosphate (DAHP) synthetase in *Escherichia coli*. J Biochem. Nov. 1994;116(5):986-90.
Gibellini et al., Biochemical characterization of the initial steps of the Kennedy pathway in Trypanosoma brucei: the ethanolamine and choline kinases. Biochem J. 2008;415:135-44. Supplemental data attached.
Goerke et al., Development of cell-free protein synthesis platforms for disulfide bonded proteins. Biotechnol Bioeng. Feb. 1, 2008;99(2):351-67. Epub Jul. 11, 2007.
Gordon-Kamm et al., Transformation of Maize Cells and Regeneration of Fertile Transgenic Plants. Plant Cell. Jul. 1990;2(7):603-618.
Gosset et al., A direct comparison of approaches for increasing carbon flow to aromatic biosynthesis in *Escherichia coli*. J Ind Microbiol. Jul. 1996;17(1):47-52.
Grabowski, Enantiopure drug synthesis: from methyldopa to imipenem to efavirenz. Chirality. 2005;17 Suppl:S249-59.
Grieco et al., .beta.-Lactam antibiotics: a formal stereocontrolled total synthesis of (.+-.)-thienamycin. J Am Chem Soc. 1984;106(21):6414-7.
Grunstein et al., Colony hybridization: a method for the isolation of cloned DNAs that contain a specific gene. Proc Natl Acad Sci U S A. Oct. 1975;72(10):3961-5.
Hamed et al., Carboxymethylproline synthase catalysed syntheses of functionalized N-heterocycles. Chem Commun (Camb). Mar. 7, 2010;46(9):1413-5. Epub Jan. 12, 2010.
Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.
Hawley et al., Compilation and analysis of *Escherichia coli* promoter DNA sequences. Nucleic Acids Res. Apr. 25, 1983;11(8):2237-55.
Herrmann, The shikimate pathway as an entry to aromatic secondary metabolism. Plant Physiol. Jan. 1995;107(1):7-12.
Hikita et al., Effects of total hydrophobicity and length of the hydrophobic domain of a signal peptide on in vitro translocation efficiency. J Biol Chem. 1992;267:4882-8.
Hikita et al., The requirement of a positive charge at the amino terminus can be compensated for by a longer central hydrophobic stretch in the functioning of signal peptides. J Biol Chem. 1992;267:12375-9.
Hodgson et al., π-Allyltricarbonyliron lactone complexes in synthesis: application to the synthesis of the β-lactam antibiotic (+)-thienamycin. J Chem Soc Chem Comm. 1984;8:494-6.
Inouye, The discovery of mRNA interferases: implication in bacterial physiology and application to biotechnology. J Cell Physiol. Dec. 2006;209(3):670-6.
Ishii et al., DBTBS: a database of *Bacillus subtilis* promoters and transcription factors. Nucleic Acids Res. Jan. 1, 2001;29(1):278-80.
Jacobi et al., Formal Total Syntheses of the β-Lactam Antibiotics Thienamycin and PS-5. J Org Chem. 1996;61(7):2413-27.
Jang et al., Sugar sensing in higher plants. Plant Cell. Nov. 1994;6(11):1665-79.
Jermutus et al., Recent advances in producing and selecting functional proteins by using cell-free translation. Curr Opin Biotechnol. Oct. 1998;9(5):534-48.
Jewett et al., An integrated cell-free metabolic platform for protein production and synthetic biology. Mol Syst Biol. 2008;4:220. Epub Oct. 14, 2008.
Jewett et al., Mimicking the *Escherichia coli* cytoplasmic environment activates long-lived and efficient cell-free protein synthesis. Biotechnol Bioeng. Apr. 5, 2005;86(1):19-26.
Kahan et al., Thienamycin, a new beta-lactam antibiotic. I. Discovery, taxonomy, isolation and physical properties. J Antibiot (Tokyo). Jan. 1979;32(1):1-12.
Kahan et al., Thienamycin: development of imipenen-cilastatin. J Antimicrob Chemother. Dec. 1983;12 Suppl D:1-35.
Kalderon et al., A short amino acid sequence able to specify nuclear location. Cell. Dec. 1984;39(3 Pt 2):499-509.
Kametani et al., Studies on the syntheses of heterocyclic compounds. 800. A formal total synthesis of (.+-.)-thienamycin and a (.+-.)-decysteaminylthienamycin derivative. J Am Chem Soc. 1980;102(6):2060-5.
Kapust et al., Tobacco etch virus protease: mechanism of autolysis and rational design of stable mutants with wild-type catalytic proficiency. Protein Eng. Dec. 2001;14(12):993-1000.
Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.

(56) References Cited

OTHER PUBLICATIONS

Kim et al., Expression, purification, and characterization of choline kinase, product of the cki gene from Saccharomyces cerevisiae. J Bio Chem. 1998;273(12):6844-6852.

Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.

Kimmel, Identification and characterization of specific clones: strategy for confirming the validity of presumptive clones. Methods Enzymol. 1987;152:507-11.

Kindle, High-frequency nuclear transformation of Chlamydomonas reinhardtii. Proc Natl Acad Sci U S A. Feb. 1990;87(3):1228-32.

Knapp et al., Cell-free production of active E. coli thioredoxin reductase and glutathione reductase. FEBS Lett. Feb. 13, 2004;559(1-3):66-70.

Knop et al., Hydroaromatic equilibration during biosynthesis of shikimic acid. J Am Chem Soc. Oct. 24, 2001;123(42):10173-82.

Ko et al., Targeting of proteins to the thylakoid lumen by the bipartite transit peptide of the 33 kd oxygen-evolving protein. EMBO J. Nov. 1989;8(11):3187-94.

Krämer et al., Metabolic engineering for microbial production of shikimic acid. Metab Eng. Oct. 2003;5(4):277-83.

Kumagai et al., Current status of oral carbapenem development. Curr Med Chem—Anti-Infective Agents. Jan. 2002;1(1):1-14.

Kunkel, Rapid and efficient site-specific mutagenesis without phenotypic selection. Proc Natl Acad Sci U S A. Jan. 1985;82(2):488-92.

Lee et al., Fermentative production of thymidine by a metabolically engineered Escherichia coli strain. Appl Environ Microbiol. Apr. 2009;75(8):2423-32. Epub Feb. 27, 2009.

Lee et al., Systems metabolic engineering of Escherichia coli for L-threonine production. Mol Syst Biol. 2007;3:149. Epub Dec. 4, 2007.

Lee, High cell-density culture of Escherichia coli. Trends Biotechnol. Mar. 1996;14(3):98-105.

Liu et al., Streamlining Escherichia coli S30 extract preparation for economical cell-free protein synthesis. Biotechnol Prog. Mar.-Apr. 2005;21(2):460-5.

Ludwig et al., Mutations affecting export and activity of cytolysin A from Escherichia coli. J Bacteriol. Aug. 2010;192(15):4001-11. Epub May 28, 2010.

Mackle et al., Role of signal peptides in targeting of proteins in cyanobacteria. J Bacteriol. Apr. 1994;176(7): 1857-64.

Mandel et al., Modular synthesis of pantetheine and phosphopantetheine. Org Lett. Dec. 23, 2004;6(26):4801-3.

Martin et al., Engineering a mevalonate pathway in Escherichia coli for production of terpenoids. Nat Biotechnol. Jul. 2003;21(7):796-802. Epub Jun. 1, 2003.

Mergulhão et al., Analysis of factors affecting the periplasmic production of recombinant proteins in Escherichia coli. J Microbiol Biotechnol. Aug. 2007;17(8):1236-41.

Mergulhão et al., Recombinant protein secretion in Escherichia coli. Biotechnol Adv. May 2005;23(3):177-202. Epub Jan. 8, 2005.

Meyerhof, New investigations in the kinetics of cell free alcoholic fermentation. Antonie Van Leeuwenhoek. Jan.-Apr. 1947;12(1-4):140-4.

Michel-Reydellet etal., Amino acid stabilization for cell-free protein synthesis by modification of the Escherichia coli genome. Metab Eng. Jul. 2004;6(3):197-203.

Muchmore et al., Crystal structure of glutamine phosphoribosylpyrophosphate amidotransferase from Escherichia coli.Protein Sci. Jan. 1998;7(1):39-51.

Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.

Murphy, Use of bacteriophage lambda recombination functions to promote gene replacement in Escherichia coli. J Bacteriol. Apr. 1998;180(8):2063-71.

Myers et al., Determination of imipenem and cilastatin in serum by high-pressure liquid chromatography. Antimicrob Agents Chemother. Jul. 1984;26(1):78-81.

Narang et al., Improved phosphotriester method for the synthesis of gene fragments. Methods Enzymol. 1979;68:90-8.

Neidhardt et al., Culture medium for enterobacteria. J Bacteriol. Sep. 1974;119(3):736-47.

Nunez et al., The Biosynthetic Gene Cluster for the β-Lactam Carbapenem Thienamycin in Streptomyces cattleya. Chem Biol. Apr. 2003;10(4):301-11.

Ono et al., Photosynthetic electron transport and phosphorylation reactions in thylakoid membranes from the blue-green alga Anacystis nidulans. Biochim Biophys Acta. Jun. 8, 1978;502(3):477-85.

Park et al., Metal-catalyzed oxidation of phenylalanine-sensitive 3-deoxy-D-arabino heptulosonate-7-phosphate synthase from Escherichia coli: inactivation and destabilization by oxidation of active-site cysteines. J Bacteriol. Mar. 1999;181(5):1636-42.

Patnaik et al., Engineering of Escherichia coli central metabolism for aromatic metabolite production with near theoretical yield. Appl Environ Microbiol. Nov. 1994;60(11):3903-8.

Pitera et al., Balancing a heterologous mevalonate pathway for improved isoprenoid production in Escherichia coli. Metab Eng. Mar. 2007;9(2):193-207. Epub Nov. 23, 2006.

Qi et al., A one-step PCR-based method for rapid and efficient site-directed fragment deletion, insertion, and substitution mutagenesis. J Virolog Meth. Apr. 2008;149(1):85-90.

Ray et al., Mutational analysis of the catalytic and feedback sites of the tryptophan-sensitive 3-deoxy-D-arabino-heptulosonate-7-phosphate synthase of Escherichia coli. J Bacteriol. Dec. 1988;170(12):5500-6.

Reider et al., Total synthesis of thienamycin: a new approach from aspartic acid. Tetra Lett. 1982;23(22):2293-6.

Reyes et al., Genomic library screens for genes involved in n-butanol tolerance in Escherichia coli. PloS One. Mar. 8, 2011;6(3):e17678.

Rodríguez et al., Identification of transcriptional activators for thienamycin and cephamycin C biosynthetic genes within the thienamycin gene cluster from Streptomyces cattleya. Mol Microbiol. Aug. 2008;69(3):633-45.

Rodríguez et al., Transcriptional organization of ThaI-regulated thienamycin biosynthetic genes in Streptomyces cattleya. J Antibiot (Tokyo). Mar. 2010;63(3):135-8. Epub Jan. 22, 2010.

Sagui et al., Enzymatic synthesis of ω-carboxy-β-hydroxy-(1)-α-amino acids. Tetrahedron. May 26, 2008;64(22):5079-84.

Salis et al., Automated design of synthetic ribosome binding sites to control protein expression. Nat Biotechnol. Oct. 2009;27(10):946-50. Epub Oct. 4, 2009.

Salzmann et al., A stereocontrolled synthesis of (+)-thienamycin. J Am Chem Soc. 1980;102(19);6161-3.

Salzmann et al., A stereocontrolled, enantiomerically specific total synthesis of thienamycin. Philos Trans R Soc Lond B Biol Sci. May 16, 1980;289(1036):191-5.

Sarath et al., Use of GFP as a reporter for the analysis of sequence-specific proteases. Curr Protoc Protein Sci. Feb. 2001;Chapter 21 Unit 9 Suppl. 26: 21.9.1-.10.

Sato et al., Poly[(R)-3-hydroxybutyrate] formation in Escherichia coli from glucose through an enoyl-CoA hydratase-mediated pathway. J Biosci Bioeng, Jan. 2007;103(1):38-44.

Schlehuber et al., Prediction and identification of a permissive epitope insertion site in the vesicular stomatitis virus glycoprotein. J Virol. May 2004;78(10):5079-87.

Schnell, Protein targeting to the thylakoid membrane. Annu Rev Plant Physiol Plant Mol Biol. Jun. 1998;49:97-126.

Scopes, Glycolysis in cell-free systems. New beer in an old bottle: Eduard Buchner and the growth of biochemical knowledge. Ed A. Cornish-Bowden. 1997;151-8.

Sheen, Metabolic repression of transcription in higher plants. Plant Cell. Oct. 1990;2(10):1027-38.

Shi et al., Molecular properties, functions, and potential applications of NAD kinases. Acta Biochim Biophys Sin (Shanghai). May 2009;41(5):352-61.

(56) References Cited

OTHER PUBLICATIONS

Shine et al., Determinant of cistron specificity in bacterial ribosomes. Nature. Mar. 6, 1975;254(5495):34-8.
Simmons et al., Translational level is a critical factor for the secretion of heterologous proteins in *Escherichia coli*. Nat Biotechnol. May 1996;14(5):629-34.
Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.
Soares et al., Periplasmic expression of human growth hormone via plasmid vectors containing the lambdaPL promoter: use of HPLC for product quantification. Protein Eng. Dec. 2003;16(12):1131-8.
Sorci et al., Nicotinamide mononucleotide synthetase is the key enzyme for an alternative route of NAD biosynthesis in Francisella tularensis.Proc Natl Acad Sci U S A. Mar. 3, 2009;106(9):3083-8. Epub Feb. 9, 2009. Supporting information attached.
Stadtman et al., Metal-catalyzed oxidation of proteins. Physiological consequences. J Biol Chem. Feb. 5, 1991;266(4):2005-8.
Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.
Stephanopoulos et al., Exploiting biological complexity for strain improvement through systems biology. Nat Biotechnol. Oct. 2004;22(10):1261-7.
Suzuki et al., Single protein production (SPP) system in *Escherichia coli*. Nat Protoc. 2007;2(7):1802-10.
Suzuki et al., Single protein production in living cells facilitated by an mRNA interferase. Mol Cell. Apr. 15, 2005;18(2):253-61.
Swartz et al., Advances in *Escherichia coli* production of therapeutic proteins. Curr Opin Biotechnol. Apr. 2011;12(2):195-201.
Swartz, Developing cell-free biology for industrial applications. J Ind Microbiol Biotechnol. Jul. 2006;33(7):476-85. Epub May 9, 2009. Review.
Sybesma et al., Increased production of folate by metabolic engineering of Lactococcus lactis. Appl Environ Microbiol. Jun. 2003;69(6):3069-76.
Tjalsma et al., Proteomics of protein secretion by *Bacillus subtilis*: separating the "secrets" of the secretome. Microbiol Mol Biol Rev. Jun. 2004;68(2):207-33.
Tracewell et al., Directed enzyme evolution: climbing fitness peaks one amino acid at a time. Curr Opin Chem Biol. Feb. 2009;13(1):3-9. Epub Feb. 25, 2009.
Tyo et al., Analysis of polyhydroxybutyrate flux limitations by systematic genetic and metabolic perturbations. Metab Eng. May 2010;12(3):187-95. Epub Oct. 30, 2009.
Van Bloois et al., Export of functional Streptomyces coelicolor alditol oxidase to the periplasm or cell surface of *Escherichia coli* and its application in whole-cell biocatalysis. Appl Microbiol Biotechnol. Jun. 2009;83(4):679-87. Epub Feb. 18, 2009.
Van Hees et al., Determination of low molecular weight organic acids in soil solution by HPLC. Talanta. Jan. 5, 1999;48(1):173-9.
Voloshin et al., Efficient and scalable method for scaling up cell free protein synthesis in batch mode. Biotechnol Bioeng. Aug. 20, 2005;91(4):516-21.
Wahl et al., Molecular hybridization of immobilized nucleic acids: theoretical concepts and practical considerations. Methods Enzymol. 1987;152:399-407.
Weaver et al., Cloning of an aroF allele encoding a tyrosine-insensitive 3-deoxy-D-arabino-heptulosonate 7-phosphate synthase. J Bacteriol. Nov. 1990;172(11):6581-4.
Welch et al., Studies on cell-free metabolism: Ethanol production by a yeast glycolytic system reconstituted from purified enzymes. J Biotechnol. 1985;2:257-73.
Wiechert et al., A universal framework for 13C metabolic flux analysis. Metab Eng. Jul. 2001;3(3):265-83.
Wiechert, 13C metabolic flux analysis. Metab Eng. Jul. 2001;3(3):195-206.
Wilen et al., Tetrahedron report No. 38: Strategies in optical resolutions. Tetrahedron. 1977;33:2725-2736.
Williamson et al., Biosynthesis of the beta-lactam antibiotic, thienamycin, by Streptomyces cattleya. J Biol Chem. Apr. 25, 1985;260(8):4637-47.
Wilson et al., The shikimic acid pathway and polyketide biosynthesis. J Indust Microbiol Biotechnol. 1998;20:299-303.
Withers et al., Identification of isopentenol biosynthetic genes from Bacillus subtilis by a screening method based on isoprenoid precursor toxicity. Appl Environ Microbiol. Oct. 2007;73(19):6277-83. Epub Aug. 10, 2007.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wylie et al., A single point mutation in ctp synthetase of chlamydia trachomatis confers resistance to cyclopentenyl cytosine. J Biol Chem. 1996;271:15393-400.
Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.
Yamaguchi et al., mRNA interferases, sequence-specific endoribonucleases from the toxin-antitoxin systems. Prog Mol Biol Transl Sci. 2009;85:467-500.
Yang et al., Export of methyl parathion hydrolase to the periplasm by the twin-arginine translocation pathway in *Escherichia coli*. J Agric Food Chem. Oct. 14, 2009;57(19):8901-5.
Yang et al., Rapid expression of vaccine proteins for B-cell lymphoma in a cell-free system Biotechnol Bioeng. Mar. 5, 2005;89(5):503-11.
Yeo et al., Plasmodium falciparum CTP:phosphocholine cytidylyltransferase expressed in *Escherichia coli*: purification, characterization and lipid regulation. Biochem J. 1997;324:903-10.
Zamboni et al., (13)C-based metabolic flux analysis. Nat Protoc. 2009;4(6):878-92. Epub May 21, 2009.
Zawada et al., Effects of growth rate on cell extract performance in cell-free protein synthesis Biotechnol Bioeng. Jul. 5, 2006;94(4):618-24.
Zawada et al., Maintaining rapid growth in moderate-density *Escherichia coli* fermentations Biotechnol Bioeng. Feb. 20, 2005;89(4):407-15.
Zhang et al., Characterization of ChpBK, an mRNA interferase from *Escherichia coli*. J Biol Chem. Jul. 15, 2005;280(28):26080-8. Epub May 18, 2005.
Zhang et al., Characterization of YafO, an *Escherichia coli* toxin. J Biol Chem. Sep. 18, 2009;284(38):25522-31. Epub Jul. 17, 2009.
Zhang et al., Efficient regeneration of transgenic plants from rice protoplasts and correctly regulated expression of the foreign gene in the plants. Theor Appl Genet. 1988;76(6):835-40.
Zhang et al., Insights into the mRNA cleavage mechanism by MazF, an mRNA interferase. J Biol Chem. Feb. 4, 2005;280(5):3143-50. Epub Nov. 10, 2004.
Extended European Search Report for EP 09836804.6 mailed Jun. 4, 2012.
Office Action, mailed Jul. 2, 2012, for U.S. Appl. No. 12/644,998.
GENBANK Submission; NIH/NCBI, Accession No. AAB59985; Ling et al.; Nov. 24, 1994.
GENBANK Submission; NIH/NCBI, Accession No. AAC73225; Blattner et al.; Sep. 1, 2011.
GENBANK Submission; NIH/NCBI, Accession No. AAC73226; Blattner et al.; Sep. 1, 2011.
GENBANK Submission; NIH/NCBI, Accession No. AAC73296; Blattner et al.; Sep. 1, 2011.
GENBANK Submission; NIH/NCBI, Accession No. AAC73346; Blattner et al.; Sep. 1, 2011.
GENBANK Submission; NIH/NCBI, Accession No. AAC73347; Blattner et al.; Sep. 1, 2011.
GENBANK Submission; NIH/NCBI, Accession No. AAC73842; Blattner et al.; Sep. 1, 2011.
GENBANK Submission; NIH/NCBI, Accession No. AAC73957; Blattner et al.; Sep. 1, 2011.
GENBANK Submission; NIH/NCBI, Accession No. AAC74746; Blattner et al.; Sep. 1, 2011.

(56) References Cited

OTHER PUBLICATIONS

GENBANK Submission; NIH/NCBI, Accession No. AAC74849; Blattner et al.; Sep. 1, 2011.
GENBANK Submission; NIH/NCBI, Accession No. AAC74924; Blattner et al.; Sep. 1, 2011.
GENBANK Submission; NIH/NCBI, Accession No. AAC75447; Blattner et al.; Sep. 1, 2011.
GENBANK Submission; NIH/NCBI, Accession No. AAC75821; Blattner et al.; Sep. 1, 2011.
GENBANK Submission; NIH/NCBI, Accession No. AAC75962; Blattner et al.; Sep. 1, 2011.
GENBANK Submission; NIH/NCBI, Accession No. AAC75963; Blattner et al.; Sep. 1, 2011.
GENBANK Submission; NIH/NCBI, Accession No. AAC76849; Blattner et al.; Sep. 1, 2011.
GENBANK Submission; NIH/NCBI, Accession No. AAC76898; Blattner et al.; Sep. 1, 2011.
GENBANK Submission; NIH/NCBI, Accession No. AAC76901; Blattner et al.; Sep. 1, 2011.
GENBANK Submission; NIH/NCBI, Accession No. AAC76995; Blattner et al.; Sep. 1, 2011.
GENBANK Submission; NIH/NCBI, Accession No. AAD38229; McGowan et al.; Jul. 14, 1999.
GENBANK Submission; NIH/NCBI, Accession No. AAD38230; McGowan et al.; Jul. 14, 1999.
GENBANK Submission; NIH/NCBI, Accession No. AAD38231; McGowan et al.; Jul. 14, 1999.
GENBANK Submission; NIH/NCBI, Accession No. ABA79923; Copeland et al.; Nov. 21, 2011.
GENBANK Submission; NIH/NCBI, Accession No. ACJ71669; Erb et al.; Dec. 10, 2008.
GENBANK Submission; NIH/NCBI, Accession No. AEW99093; Ou et al.; Dec. 29, 2011.
GENBANK Submission; NIH/NCBI, Accession No. AEW99097; Ou et al.; Dec. 29, 2011.
GENBANK Submission; NIH/NCBI, Accession No. AEW99098; Ou et al.; Dec. 29, 2011.
GENBANK Submission; NIH/NCBI, Accession No. BAA22406; Mori et al.; Sep. 20, 1997.
GENBANK Submission; NIH/NCBI, Accession No. BAB67276; Kawarabayasi et al.; Aug. 17, 2011.
GENBANK Submission; NIH/NCBI, Accession No. CAD18973; Nunez et al.; Apr. 15, 2005.
GENBANK Submission; NIH/NCBI, Accession No. CAD18975; Nunez et al.; Apr. 15, 2005.
GENBANK Submission; NIH/NCBI, Accession No. CAD18981; Nunez et al.; Apr. 15, 2005.
GENBANK Submission; NIH/NCBI, Accession No. CAD18985; Nunez et al.; Apr. 15, 2005.
GENBANK Submission; NIH/NCBI, Accession No. CAD18990; Nunez et al.; Apr. 15, 2005.
UniProtKB/Swiss-Prot; Accession No. P28269; Yonaha et al.; Jul. 11, 2012.
Fischer et al., Metabolic flux profiling of *Escherichia coli* mutants in central carbon metabolism using GC-MS. Eur J Biochem. Mar. 2003;270(5):880-91.
Flores et al., Analysis of carbon metabolism in *Escherichia coli* strains with an inactive phosphotransferase system by (13)C labeling and NMR spectroscopy. Metab Eng. Apr. 2002;4(2):124-37.
Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.
Fradejas et al., The control of shikimic acid synthesis by tyrosine and phenylalamine. Biochem Biophys Res Commun. Jul. 26, 1961;5:320-3.
Kern et al., Engineering primary metabolic pathways of industrial micro-organisms. J Biotechnol. Mar. 30, 2007;129(1):6-29. Epub Dec. 2, 2006.

Luli et al., Comparison of growth, acetate production, and acetate inhibition of *Escherichia coli* strains in batch and fed-batch fermentations. Appl Environ Microbiol. Apr. 1990;56(4):1004-11.
Meynial-Salles et al., New tool for metabolic pathway engineering in *Escherichia coli*: one-step method to modulate expression of chromosomal genes. Appl Environ Microbiol. Apr. 2005;71(4):2140-4.
Niu et al., Benzene-free synthesis of adipic acid. Biotechnol Prog. Mar.-Apr. 2002;18(2):201-11.
Sauer et al., The soluble and membrane-bound transhydrogenases UdhA and PntAB have divergent functions in NADPH metabolism of *Escherichia coli*. J Biol Chem. Feb. 20, 2004;279(8):6613-9. Epub Dec. 3, 2003.
Wang et al., Programming cells by multiplex genome engineering and accelerated evolution. Nature. Aug. 13, 2009;460(7257):894-8. Epub Jul. 26, 2009.
Collins-Racie et al., Production of recombinant bovine enterokinase catalytic subunit in *Escherichia coli* using the novel secretory fusion partner DsbA. Biotechnology (N Y). Sep. 1995;13(9):982-7.
International Search Report and Written Opinion for PCT/US2012/054195, mailed Apr. 12, 2013.
International Preliminary Report on Patentability for PCT/US2012/054195, mailed Mar. 20, 2014.
International Preliminary Report on Patentability for PCT/US2011/035639, mailed Nov. 22, 2012.
International Search Report and Written Opinion for PCT/US2011/049997, mailed Dec. 13, 2011.
International Preliminary Report on Patentability for PCT/US2011/049997, mailed Mar. 14, 2013.
International Search Report and Written Opinion for PCT/US2013/077238, mailed May 19, 2014.
Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Paul et al., Photophosphorylation in bacterial chromatophores entrapped in alginate gel: Improvement of the physical and biochemical properties of gel beads with barium as gel-inducing agent. Enzyme Microb Technol. 1980;2(4):281-87.
Peralta-Yahya et al., Microbial engineering for the production of advanced biofuels. Nature. Aug. 16, 2012;488(7411):320-8. doi: 10.1038/nature11478.
Srinivasan et al., The Enzymatic Synthesis of Shikimic Acid From D-Erythrose-4-Phosphate and Phosphoenolpyruvate1,2,3. J. Am. Chem. Soc. 1955;77(18):4943-4944.
Swartz, Transforming biochemical engineering with cell-free biology. AIChE J. 2012;58(1):5-13.
International Search Report and Written Opinion for PCT/US2014/041009, mailed Sep. 10, 2014.
Invitation to Pay Additional Fees for PCT/US2014/049805, mailed Nov. 14, 2014.
International Search Report for PCT/US2014/049805, mailed Feb. 16, 2015.
[No Author Listed] Crude Lysate. Wikipedia entry for Crude Lysate, http://en.wikipedia.org/wild/Crude_lysate downloaded on Mar. 3, 2015. Page Last Modified on Nov. 3, 2013. 1 page.
Bujara et al., Exploiting cell-free systems: Implementation and debugging of a system of biotransformations. Biotechnol Bioeng. Jun. 15, 2010;106(3):376-89. doi: 10.1002/bit.22666.
Danese et al., Targeting and assembly of periplasmic and outer-membrane proteins in *Escherichia coli*. Annu Rev Genet. 1998;32:59-94.
Egan et al., Transketolase kinetics. The slow reconstitution of the holoenzyme is due to rate-limiting dimerization of the subunits. J Biol Chem. May 25, 1981;256(10):4877-83.
Eser et al., Target-directed proteolysis in vivo. Methods Enzymol. 2007;421:68-83.
Goerke et al., Cell-free metabolic engineering promotes high-level production of bioactive Gaussia princeps luciferase. Metab Eng. May-Jul. 2008;10(3-4):187-200. doi: 10.1016/j.ymben.2008.04.001. Epub May 2, 2008.
Jenny et al., A critical review of the methods for cleavage of fusion proteins with thrombin and factor Xa. Protein Expr Purif. Sep. 2003;31(1):1-11.

(56) References Cited

OTHER PUBLICATIONS

Krutsakorn et al., In vitro production of n-butanol from glucose. Metab Eng. Nov. 2013;20:84-91. doi: 10.1016/j.ymben.2013.09.006. Epub Sep. 19, 2013.

Ninh et al., Assembly and multiple gene expression of thermophilic enzymes in *Escherichia coli* for in vitro metabolic engineering. Biotechnol Bioeng. Jul. 26, 2014. doi: 10.1002/bit.25338.

Ye et al., Synthetic metabolic engineering-a novel, simple technology for designing a chimeric metabolic pathway. Microb Cell Fact. Sep. 6, 2012;11:120. doi: 10.1186/1475-2859-11-120.

Extended European Search Report for EP09835395.6 mailed Mar. 16, 2016.

International Preliminary Report on Patentability for PCT/US2013/077238 mailed Jul. 2, 2015.

International Preliminary Report on Patentability for PCT/US2014/049805, mailed Feb. 18, 2016.

International Preliminary Report on Patentability for PCT/US2014/041009, mailed Dec. 17, 2015.

Invitation to Pay Additional Fees for PCT/US2016/023173, mailed Jul. 8, 2016.

GenBank Accession No. AAC43119. 1993. 4 pages.

Blattner et al., Analysis of the *Escherichia coli* genome. IV. DNA sequence of the region from 89.2 to 92.8 minutes. Nucleic Acids Res. Nov. 25, 1993;21(23):5408-17.

Chisti et al., Disruption of microbial cells for intracellular products. Enzyme Micro Technol 1986;8(4):194-204. doi 10.1016/0141-0229(86)90087-6.

Daube et al., Cell-free co-synthesis of protein nanoassemblies: tubes, rings, and doughnuts. Nano Lett. Mar. 2007;7(3):638-41. Epub Feb. 2, 2007.

Ehrmann et al., TnTIN and TnTAP: mini-transposons for site-specific proteolysis in vivo. Proc Natl Acad Sci U S A. Nov. 25, 1997;94(24):13111-5.

Fujio et al., Production of ATP from Adenine by Brevibacterium ammoniagenes, J Ferment Technol. 1983;61(3):261-267.

Hryniewicz et al., Sulfate and thiosulfate transport in *Escherichia coli* K-12: identification of a gene encoding a novel protein involved in thiosulfate binding. J Bacteriol. Jun. 1990;172(6):3358-66.

Kang et al., Enhanced biodegradation of toxic organophosphate compounds using recombinant *Escherichia coli* with sec pathway-driven periplasmic secretion of organophosphorus hydrolase. Biotechnol Prog. Mar.-Apr. 2006;22(2):406-10.

Kawarasaki et al., Prolonged cell-free protein synthesis in a batch system using wheat germ extract.Biosci Biotechnol Biochem. Oct. 1994;58(10):1911-3.

Kim et al., Regeneration of adenosine triphosphate from glycolytic intermediates for cell-free protein synthesis.Biotechnol Bioeng. Aug. 20, 2001;74(4):309-16.

Klemme, Photoproduction of hydrogen by purple bacteria:A critical evaluation of the rate limiting enzymatic steps. J Bioscience 1993;48 482-87.

Liu et al., Combined biosynthetic pathway for de novo production of UDP-galactose: catalysis with multiple enzymes immobilized on agarose beads. Chembiochem. Apr. 2, 2002;3(4):348-55.

Mayes, Metabolism of Glycogen. In: Harper's Biochemistry—a LANGE medical book. 1990. Twenty-second edition. Murray et al., Eds. Chapter 20: 171-178.

Noireaux et al., Principles of cell-free genetic circuit assembly. Proc Natl Acad Sci U S A. Oct. 28, 2003;100(22):12672-7. Epub Oct. 14, 2003.

Pines et al., Expression and secretion of proteins in *E. coli*. Mol Biotechnol. Aug. 1999;12(1):25-34.

Schierle et al., The DsbA signal sequence directs efficient, cotranslational export of passenger proteins to the *Escherichia coli* periplasm via the signal recognition particle pathway. J Bacteriol. Oct. 2003;185(19):5706-13.

Schultheisz et al., Pathway engineered enzymatic de novo purine nucleotide synthesis. ACS Chem Biol. Aug. 15, 2008;3(8):499-511. doi: 10.1021/cb800066p.

Scopes, Studies with a reconstituted muscle glycolytic system. The anaerobic glycolytic response to simulated tetanic contraction. Biochem J. Jan. 1974;138(1):119-23.

Spirin, High-throughput cell-free systems for synthesis of functionally active proteins.Trends Biotechnol. Oct. 2004;22(10):538-45. With Supplementary data.

Sroga et al., Periplasmic expression as a basis for whole cell kinetic screening of unnatural enzyme reactivities. Methods Enzymol. 2004;388:145-56.

Stapon et al., Carbapenem biosynthesis: confirmation of stereochemical assignments and the role of CarC in the ring stereoinversion process from L-proline. J Am Chem Soc. Jul. 16, 2003;125(28):8486-93.

Swartz, Universal cell-free protein synthesis. Nat Biotechnol. Aug. 2009;27(8):731-2. doi: 10.1038/nbt0809-731.

Thöny-Meyer et al., Translocation to the periplasm and signal sequence cleavage of preapocytochrome c depend on sec and lep, but not on the ccm gene products. Eur J Biochem. Jun. 15, 1997;246(3):794-9.

Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.

Zhao et al., A novel high-throughput screening method for microbial transglutaminases with high specificity toward Gln141 of human growth hormone. J Biomol Screen. Feb. 2010;15(2):206-12. doi: 10.1177/1087057109356206. Epub Jan. 19, 2010.

\* cited by examiner

| | | REACTIONS / ENZYMES / CORRESPONDING E.coli GENES | | | | | |
|---|---|---|---|---|---|---|---|
| no. | EC | enzyme | Ec gene | no. | EC | enzyme | Ec gene |
| 1. | 2.7.1.2 | glucokinase | glk | 13. | 2.7.2.3 | phosphoglycerate kinase | pgk |
| 2. | 1.1.1.49 | glucose-6-phosphate dehydrogenase | zwf | 14. | 5.4.2.1 | phosphoglycerate mutase | gpmA |
| 3. | 3.1.1.31 | 6-phosphogluconolactonase | pgl | 15. | 4.2.1.11 | enolase | eno |
| 4. | 1.1.1.44 | 6-phosphogluconate dehydrogenase | gnd | 16. | 2.7.1.40 | pyruvate kinase | pykAF |
| 5. | 5.3.1.6 | ribose-5-phosphate isomerase | rpiA | 17. | 2.5.1.54 | DAHP synthetase | aroFGH |
| 6. | 5.3.1.1 | ribulose phosphate epimerase | rpe | 18. | 4.2.3.4 | 3-dehydroquinate synthase | aroB |
| 7. | 2.2.1.1 | transketolase | tktA | 19. | 4.2.1.10 | 3-dehydroquinate dehydratase | aroD |
| 8. | 2.2.1.2 | transaldolase | talB | 20. | 1.1.1.25 | shikimate dehydrogenase | aroE |
| 9. | 5.3.1.9 | phosphoglucose isomerase | pgi | 21. | 2.7.1.71 | shikimate kinase | aroKL |
| 10. | 2.7.1.11 | phosphofructokinase | pfkA | 22. | 1.6.1.1 | nucleotide transhydrogenase | sthA |
| 11. | 4.1.2.13 / 5.3.1.1 | fructose bisphosphate aldolase / triose phosphate isomerase | fbaA / tpiA | 23. | | respiration/oxidative phosphorylation system | |
| 12. | 1.2.1.12 | glyceraldehyde-3-phosphate dehydrogenase | gapA | | | | |

Figure 1B

| INTERMEDIATE REACTANT/PRODUCT INVENTORY ||||
|---|---|---|---|
| CONSUMED || PRODUCED ||
| −3 glucose | $3C_6H_{12}O_6$ | +2 shikimate | $2C_7H_9O_5$ |
| −2 ATP | $2C_{10}H_{13}N_5O_{13}P_3$ | +2 ADP | $2C_{10}H_{12}N_5O_{10}P_2$ |
| −2 NAD⁺ | $2C_{21}H_{26}N_7O_{14}P_2$ | +2 NADH | $2C_{21}H_{27}N_7O_{14}P_2$ |
| −6 NADP⁺ | $6C_{21}H_{25}N_7O_{17}P_3$ | +6 NADPH | $6C_{21}H_{26}N_7O_{17}P_3$ |
| −2 $H_2O$ | $2H_2O$ | +4 $CO_2$ | $4CO_2$ |
| | | +2 Pi | $2HPO_4$ |
| | | +14 H⁺ | 14H⁺ |

Figure 1C

| REACTIONS / ENZYMES / CORRESPONDING E.coli GENES ||||||
|---|---|---|---|---|---|
| nxn | EC | enzyme | Ec gene | nxn | EC | enzyme | Ec gene |
| 1. | 2.7.1.2 | glucokinase | glk | 12. | 5.3.1.6 | ribose-5-phosphate isomerase | rpiA |
| 2. | 5.3.1.9 | phosphoglucose isomerase | pgi | 13. | 2.2.1.1 | transketolase | tktA |
| 3. | 2.7.1.11 | phosphofructokinase | pfkA | 14. | 2.2.1.2 | transaldolase | talB |
| 4. | 4.1.2.13 5.3.1.1 | fructose bisphosphate aldolase triose phosphate isomerase | fbaA tpiA | 15. | 2.5.1.54 | DAHP synthetase | aroFGH |
| 5. | 1.2.1.12 | glyceraldehyde 3-phosphate dehydrogenase | gapA | 16. | 4.2.3.4 | 3-dehydroquinate synthase | aroB |
| 6. | 2.7.2.3 | phosphoglycerate kinase | pgk | 17. | 4.2.1.10 | 3-dehydroquinate dehydratase | aroD |
| 7. | 5.4.2.1 | phosphoglycerate mutase | gpmA | 18. | 1.1.1.25 | shikimate dehydrogenase | aroE |
| 8. | 4.2.1.1 | enolase | eno | 19. | 2.7.1.71 | shikimate kinase | aroKL |
| 9. | 2.7.1.40 | pyruvate kinase | pykAF | 20. | 1.6.1.1 | nucleotide transhydrogenase | sthA |
| 10. | 2.2.1.1 | transketolase | tktA | 21. | | respiration/oxidative phosphorylation system | |
| 11. | 5.1.3.1 | ribulose phosphate 3-epimerase | rpe | | | | |

Figure 2B

| INTERMEDIATE REACTANT/PRODUCT INVENTORY ||||
|---|---|---|---|
| CONSUMED || PRODUCED ||
| -7 glucose | $7C_6H_{12}O_6$ | +6 shikimate | $6C_7H_9O_5$ |
| -6 ATP | $6C_{10}H_{13}N_5O_{13}P_3$ | +6 ADP | $6C_{10}H_{12}N_5O_{10}P_2$ |
| -6 NAD$^+$ | $6C_{21}H_{26}N_7O_{14}P_2$ | +6 NADH | $6C_{21}H_{27}N_7O_{14}P_2$ |
| -6 NADPH | $6C_{21}H_{26}N_7O_{17}P_3$ | +6 NADP$^+$ | $6C_{21}H_{25}N_7O_{17}P_3$ |
| | | +6 $H_2O$ | $6H_2O$ |
| | | +6 Pi | $6HPO_4$ |
| | | +18 H$^+$ | $18H^+$ |

Figure 2C

SEQUENCE LISTING

```
<160> NUMBER OF SEQ ID NOS: 4

<210> SEQ ID NO 1
<211> LENGTH: 7
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa is Gly or Ser

<400> SEQUENCE: 1

Glu Asn Leu Tyr Phe Gln Xaa
1               5

<210> SEQ ID NO 2
<211> LENGTH: 5
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa is Gly or Ser
```

```
<400> SEQUENCE: 2

Gly Ala Arg Arg Xaa
1               5

<210> SEQ ID NO 3
<211> LENGTH: 6
<212> TYPE: PRT
<213> ORGANISM: Homo sapiens

<400> SEQUENCE: 3

Leu Val Pro Arg Gly Ser
1               5

<210> SEQ ID NO 4
<211> LENGTH: 4
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa is Glu or Asp

<400> SEQUENCE: 4

Ile Xaa Gly Arg
1
```

METHODS FOR CONTROL OF FLUX IN METABOLIC PATHWAYS

RELATED APPLICATIONS

The present application is a national stage filing under 35 U.S.C. §371 of international PCT application, PCT/US2009/067841, filed Dec. 14, 2009, which claims priority under 35 U.S.C. §119(e) to U.S. provisional application, U.S. Ser. No. 61/201,783, filed Dec. 15, 2008, each of which is incorporated herein by reference.

BACKGROUND TO THE INVENTION

Metabolic engineering has allowed production of chemicals of commercial interest through manipulation of biochemical reactions in the cell. However, all organisms have evolved with the objective of replicating their genetic material and, therefore, production of chemicals that may be of commercial interest may conflict with essential cellular goals. For example, diversion of nutrients and energy for the production of a compound may result in a shortage of those substrates for production of biomass. The organism that is engineered may either evolve away from producing the compound of interest or grow sub-optimally.

To address this issue, systems have been engineered for stationary phase-associated production of a compound of interest. However, a limitation is that stationary phase itself elicits a series of responses that are aimed at protecting the cell during non-growing conditions, so cellular resources are still needed for combating stress and preserving the stationary-phase phenotype. This effect may be pronounced when the product of interest is itself toxic or induces a stress response.

Recently, the development of cell-free systems has allowed for the in vitro production of proteins (for a review see Swartz (2006) J Ind Microbiol Biotechnol 33:476-85). A cell-free platform may also be used to produce metabolites of interest through coordinated expression of proteins in a pathway. The procedure entails growing a biomass of cells, opening the cells to liberate the cytoplasmic components, removing the genomic DNA, and using the genome-free machinery to produce a user-specified set of enzymes to serve as biocatalysts. This presents a unique opportunity for producing an environment that resembles stationary phase production systems but free of stress or other responses, although a limitation may be relatively slow kinetics of the set of reactions, given that diffusion of intermediates from one enzyme into the next is needed for a pathway to work.

Publications

International Patent Application no. WO/2007/137144; Inouye (2006) J Cell Physiol 209:670-6; Suzuki et al. (2007) Nat Protoc 2:1802-10; Suzuki et al. (2005) Mol Cell 18:253-61.

SUMMARY OF THE INVENTION

Compositions and methods are provided for controlling metabolic pathway flux through manipulation of targeted enzymes involved in a pathway of interest, including manipulation to maintain or alter the cellular concentration of key pathway enzymes during a cell growth phase, followed by manipulation to (a) increase concentrations of key pathway enzymes and/or (b) decrease concentrations of competitive enzymes during a production phase, where the product of the pathway of interest is produced. The cell growth phase necessarily involves intact cells, while the production phase is may be performed with intact cells or lysates of such cells.

Specifically, the microbial cells are genetically modified, such that mRNA encoding enzymes involved in the pathway of interest are resistant to the ribonuclease activity of interferases, also referred to as TA toxins. After induction of interferase expression, the microbial cells substantially lack new polypeptide synthetic activity, except for enzymes involved in a pathway of interest, referred to herein as cells in a metabolically frozen state. The microbial cells may be prokaryotic or eukaryotic.

Generally a plurality of enzyme coding sequences in a single pathway are modified, usually at least two coding sequences, at least three coding sequences, or more. Generally one or more of the modified sequences control flux through the pathway, e.g. by catalyzing an initial diversion of a central metabolite to a pathway of interest, by catalyzing a rate-limiting step of the pathway, by controlling the production of an input substrate to the pathway, etc. Such modified coding sequence may be referred to as interferase resistant pathway enzyme sequences.

In some embodiments the microbial cells express endogenous interferase genes. In other embodiments, interferase coding sequences are introduced into the microbial cells. Interferase coding sequences may be obtained, for example, from sources such as *Mycobacterium tuberculosis* and *Myxococcus xanthus*. A metabolically-frozen state is induced by one or both of (a) expression of TA toxins, usually exogenous TA toxins; and (b) attenuation of TA antitoxins.

In some embodiments of the invention, expression of the plurality of enzymes in the pathway of interest is inducible. In such embodiments, the induction of a metabolically frozen state may be coordinated with induction of expression of the plurality of enzymes in the pathway of interest. Following induction, the cell continues to produce only the enzymes in the pathway of interest, providing a benefit for the synthesis of metabolites of the pathway. Only the set of desired enzymes continues to be produced, but without the limitation of stress responses to the cell and providing substrate channeling through the pathway by the close proximity of enzymes in the cell.

Optionally, in some embodiments of the invention, one or more enzymes that compete for substrates of enzymes in the pathway of interest are genetically altered to comprise at least one cleavage site for a site-specific protease. Generally in such embodiments, a further genetic modification is made such that the cell expresses an interferase resistant form of the cognate site-specific protease. In some embodiments, expression of the cognate site-specific protease is coordinately induced with expression of the enzymes of the pathway of interest.

In some embodiments, methods are provided for producing a product of interest at a high flux rate, the method comprising: growing cells that are genetically modified to coordinately induce interferase activity, which substantially ablates new polypeptide synthesis by cleavage of mRNA, and interferase resistant enzymes in a pathway of interest to a desired density; inducing interferase activity and expression of the interferase resistant enzymes; lysing the cells; and producing the product of the pathway in a cell-free system comprising the lysate. Additional substrate, nutrients, cofactors, buffers, reducing agents, ATP generating systems, etc. may be added to the cell-free system. In an alternative embodiment the cells are grown to a desired density; interferase activity and expression of the interferase resistant enzymes is induced; and the product of the pathway is produced in a cellular environment.

In other embodiments, the genetically modified cell is provided. In another embodiment, lysates of such a genetically modified cell are provided, which lysate may be combined with one or more of substrate, nutrients, cofactors, buffers, reducing agents, ATP generating systems, etc. to generate a cell-free system for producing a product of interest.

BRIEF DESCRIPTION OF THE FIGURES

FIGS. 1A-1C provide a metabolic scheme A for production of shikimic acid.
FIGS. 2A-2C provide a metabolic scheme B for production of shikimic acid.

DETAILED DESCRIPTION OF THE EMBODIMENTS

Figure 1A:
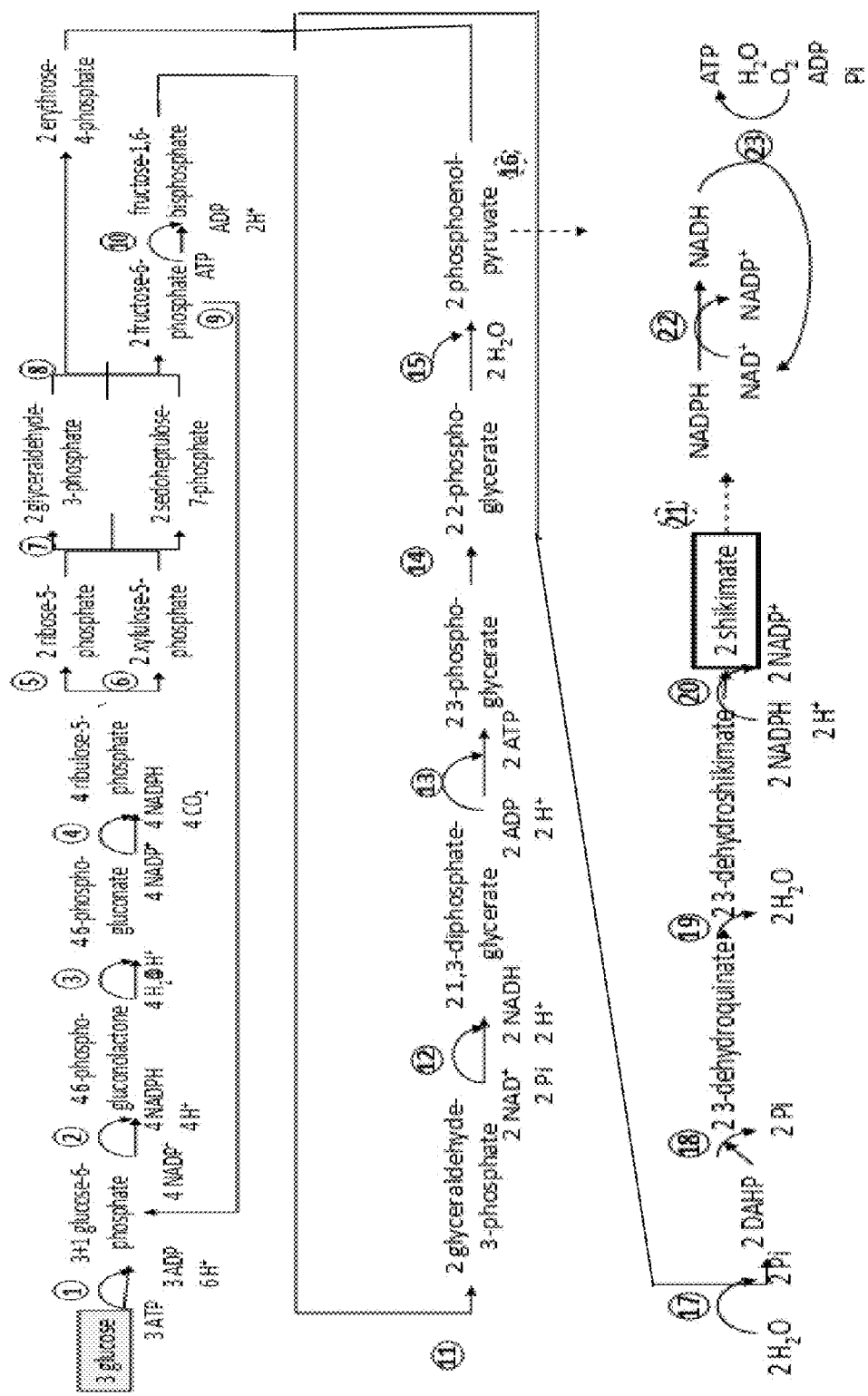

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in this section is contrary to or otherwise inconsistent with a definition set forth in the patents, applications, published applications and other publications that are incorporated herein by reference, the definition set forth in this section prevails over the definition that is incorporated herein by reference.

Citation of publications or documents is not intended as an admission that any of such publications or documents are pertinent prior art, nor does it constitute any admission as to the contents or date of these publications or documents.

As used herein, "a" or "an" means "at least one" or "one or more" unless otherwise indicated.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Host cells of interest for pathway engineering include a wide variety of heterotrophic and autotrophic microorganisms, including bacteria, fungi and protozoans. Species of interest include, without limitation, S. cerevisiae, E. coli, Picchia pastoris, etc.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Flux. The term "flux" as used herein refers to the rate that molecules pass through a pathway or reaction of interest. Among the factors that control flux are rate of catalysis of enzymes in the pathway, the availability of substrate, the concentration of enzymes in a cell, the proximity of enzymes in a pathway, etc.

While a high rate of flux through a pathway of interest is desirable, at the same time it can create toxicity issues if a product not normally accumulated at high levels in the cell is produced at a high rate. A stressed cell produces a number of proteins undesirable for maintaining active biocatalysis, such as nucleases, heat shock proteins, proteases and the like.

The methods of the invention provide a means of controlling flux through a pathway, such that a healthy cell, with substantially normal physiology, can be grown to high density, following which the concentration of enzymes involved in a pathway is modulated to result in an increase in the pathway flux, and accumulation of a desired product. Modulation of enzyme concentration is accomplished by inducing interferase expression, while protecting the mRNA of key pathway enzymes from degradation by the interferase. In this manner the key pathway enzymes are increased in concentration, while stress response genes are not expressed. In combination or as an alternative approach, competitive enzymes that reduce pathway flux or accumulation of the desired product may be engineered to contain a sequence specific protease cleavage site, where expression of the protease is induced in the cells at a selected time.

Methods of determining flux rates are known and used in the art, for example as described by Wiechert et al. (2001) Metab. Eng. 3, 265-283, A universal framework for 13C metabolic flux analysis", and Metab Eng. 2001 July; 3(3): 195-206; or metabolic engineering texts such as Lee and Papoutsakis, 1999, Stephanopoulos, Aristidou, Nielsen, 1998, Nielsen and Eggeling, 2001, each herein specifically incorporated by reference. Flux may be calculated from measurable quantities using techniques such as metabolic flux analysis (MFA), for example by direct measurement of the conversion of isotopically labeled substrate.

Enzyme Pathway: As used herein, the term "enzyme pathway" or "pathway of interest" refers to a cellular system for converting a substrate to a product of interest, where the system comprises a plurality of enzymes and may additionally comprise substrates acted upon by one or more of the enzymes, products of the enzyme-catalyzed reaction, cofactors utilized by the enzymes, and the like. The system may be present in an intact cell, or in a lysate of a cell. Many metabolic pathways are known and have been described in microbial systems, and are accessible in public databases. For example, a number of reference books are available, including, inter alia, The Metabolic Pathway Engineering Handbook (2009), ed. C. Smolke, CRC, ISBN-10: 1420077651 and 1439802963; Metabolic Engineering: Principles and Methodologies (1998) Stephanopoulos, Academic Press ISBN-10: 0126662606, Greenberg D M. Metabolic Pathways: Energetics, tricarboxylic acid cycle, and carbohydrates. Academic Press; 1967; Greenberg M. Metabolic pathways. Academic Press; 1968; Greenberg D M. Metabolic pathways. Academic; 1970; and Greenberg D M, Vogel H J. Metabolic pathways. Academic; 1971, each herein specifically incorporated by reference.

Pathways of interest include, without limitation, pathways involved in carbohydrate, amino acid, nucleic acid, steroid, and fatty acid metabolism, and may include synthesis of antibiotics, e.g. actinomycin, bleomycin, rifamycin, chloramphenicol, tetracycline, lincomycin, erythromycin, streptomycin, cyclohexamide, puromycin, cycloserine, bacitracin, penicillin, cephalosporin, vancomycin, polymyxin, and gramicidin; biosurfactants e.g. rhamnolipids, sophorolipids, glycolipids, and lipopeptides; biological fuels e.g. bioethanol, biodiesel, and biobutanol; amino acids e.g. L-glutamate, L-lysine, L-phenylalanine, L-aspartic acid, L-isoleucine, L-valine, L-tryptophan, L-proline (hydroxyproline), L-threonine, L-methionine, and D-p-hydroxyphenylglycine; organic acids e.g. citric acid, lactic acid, gluconic acid, acetic acid, propionic acid, succinic acid, fumaric acid, and itaconic acid; fatty acids e.g. arachidonic acid, polyunsaturated fatty acid (PUBA), and γ-linoleic acid; polyols e.g. glycerol, mannitol, erythritol, and xylitol; flavors and fragrances e.g. vanillin, benzaldehyde, dixydroxyacetone, 4-(R)-decanolide, and 2-actyl-1-pyrroline; nucleotides e.g. 5'-guanylic acid and 5'-inosinic acid; vitamins e.g. vitamin C, vitamin F, vitamin B2, provitamin D2, vitamin B12, folic acid, nicotinamide, biotin, 2-keto-L-gulonic acid, and provitamin Q10; pigments e.g. astaxathin, β-carotene, leucopene, monascorubrin, and rubropunctatin; sugars and polysaccharides e.g. ribose, sorbose, xanthan, gellan, and dextran; biopolymers and plastics e.g. polyhydroxyalkanoates (PHA), poly-γ-glutamic acid, and 1,3-propanediol; and the like as known in the art.

A number of reactions may be catalyzed by enzymes in pathways of interest. Broad classes, which can be identified by enzyme classification number, provided in parentheses, include (EC 1) oxidoreductases, e.g. dehydrogenases, oxidases, reductases, oxidoreductases, synthases, oxygenases, monooxygenases, dioxygenases, lipoxygenases, hydrogenases, transhydrogenases, peroxidases, catalases, epoxidases, hydroxylases, demethylases, desaturases, dismutases, hydroxyltransferases, dehalogenases, deiodinases, etc.; (EC2) transferases, e.g. Transaminases, kinases, dikinases, methyltransferases, hydroxymethyltransferases, formyltransferases, formiminotransferases, carboxytransferases, carbamoyltransferases, amidinotransferases, transaldolases, transketolases, acetyltransferases, acyltransferases palmitoyltransferases, succinyltransferases, malonyltransferases, galloyltransferases, sinapoyltransferases, tigloyltransferases, tetradecanoyltransferases, hydroxycinnamoyltransferases, feruloyltransferases, mycolyltransferases, benzoyltransferases, piperoyltransferases, trimethyltridecanoyltransferase, myristoyltransferases, coumaroyltransferases, thiolases, aminoacyltransferases, phosphorylases, hexosyltransferases, pentosyltransferases, sialyltransferases, pyridinylases, diphosphorylases, cyclotransferases, sulfurylases, adenosyltransferases, carboxyvinyltransferases, isopentenyltransferases, aminocarboxypropyltransferases, dimethylallyltransferases, farnesyltranstransferases, hexaprenyltranstransferases, decaprenylcistransferases, pentaprenyltranstransferases, nonaprenyltransferases, geranylgeranyltransferases, aminocarboxypropyltransferases, oximinotransferases, purinetransferases, phosphodismutases, phosphotransferases, nucleotidyltransferases, polymerases, cholinephosphotransferases, phosphorylmutases, sulfurtransferases, sulfotransferases, CoA-transferases, etc.; (EC3) hydrolases, e.g. lipases, esterases, amylases, peptidases, hydrolases, lactonases, deacylases, deacetylases, pheophorbidases, depolymerases, thiolesterases, phosphatases, diphosphatases, triphosphatases, nucleotidases, phytases, phosphodiesterases, phospholipases, sulfatases, cyclases, oligonucleotidases, ribonucleases, exonucleases, endonucleases, glycosidases, nucleosidases, glycosylases, aminopeptidases, dipeptidases, carboxypeptidases, metallocarboxypeptidases, omega-peptidases, serine endopeptidases, cystein endopeptidases, aspartic endopeptidases, metalloendopeptidases, threonine endopeptidases, aminases, amidases, desuccinylases, deformylases, acylases, deiminases, deaminases, dihydrolases, cyclohydrolases, nitrilases, ATPases, GTPases, halidases, dehalogenases, sulfohydrolases, etc.; (EC 4) lyases, e.g. decarboxylases, carboxylases, carboxykinases, aldolases, epoxylyases, oxoacid-lyases, carbon-carbon lyases, dehydratases, hydratases, synthases, endolyases, exolyases, ammonia-lyases, amidine-lyases, amine-lyases, carbon-sulfur lyases, carbon-halide lyases, phosphorus-oxygen lyases, dehydrochlorinases, etc.; (EC 5) isomerases, e.g. isomerases, racemases, mutases, tautomerases, phosphomutases, phosphoglucomutases, aminomutases, cycloisomerase, cyclases, topoisomerases, etc.; and (EC 6) ligases, e.g. synthetases, tNRA-ligases, acid-thiol ligases, amide synthases, peptide synthases, cycloligases, carboxylases, DNA-ligases, RNA-ligases, cyclases, etc.

More specific classes include, without limitation oxidoreductases, including those (EC 1.1) acting on the CH—OH group of donors, and an acceptor; (EC 1.2) Acting on the aldehyde or oxo group of donors, and an acceptor; (EC 1.3) Acting on the CH—CH group of donors, and an acceptor; (EC 1.4) Acting on the CH—NH2 group of donors, and an acceptor; (EC 1.5) Acting on the CH—NH group of donors, and an acceptor; (EC 1.6) Acting on NADH or NADPH, and an acceptor; (EC 1.7) Acting on other nitrogenous compounds as donors, and an acceptor; (EC 1.8) Acting on a sulfur group of donors, and an acceptor; (EC 1.9) Acting on a heme group of donors, and an acceptor; (EC 1.1) Acting on diphenols and related substances as donors, and an acceptor; (EC 1.11) Acting on a peroxide as acceptor; (EC 1.12) Acting on hydrogen as donor, and an acceptor; (EC 1.13) Acting on single donors with incorporation of molecular oxygen, incorporating one or two oxygen atoms; (EC 1.14) Acting on paired donors, with incorporation or reduction of molecular oxygen, with the donor being 2-oxoglutarate, NADH, NADPH, reduced flavin, flavoprotein, pteridine, iron-sulfur protein, ascorbate, etc.; (EC 1.15) Acting on superoxide radicals as acceptor; (EC 1.16) Oxidising metal ions, and an acceptor; (EC 1.17) Acting on CH or CH2 groups, and an acceptor; (EC 1.18) Acting on iron-sulfur proteins as donors, and an acceptor; (EC 1.19) Acting on reduced flavodoxin as donor, and an acceptor; (EC 1.20) Acting on phosphorus or arsenic in donors, and an acceptor; (EC 1.21) Acting on X—H and Y—H to form an X—Y bond, and an acceptor; where acceptors for each donor category may include, without limitation: NAD, NADP, heme protein, oxygen, disulfide, quinone, an iron-sulfur protein, a flavin, a nitrogenous group, a cytochrome, dinitrogen, and $H^+$.

Transferases include those: (EC 2.1) Transferring one-carbon groups; (EC 2.2) Transferring aldehyde or ketonic groups; (EC 2.3) Acyltransferases; (EC 2.4) Glycosyltransferases; (EC 2.5) Transferring alkyl or aryl groups, other than methyl groups; (EC 2.6) Transferring nitrogenous groups; (EC 2.7) Transferring phosphorus-containing groups; (EC 2.8) Transferring sulfur-containing groups; (EC 2.9) Transferring selenium-containing groups.

Hydrolases include those: (EC 3.1) Acting on ester bonds; (EC 3.2) Glycosylases; (EC 3.3) Acting on ether bonds; (EC 3.4) Acting on peptide bonds (peptidases); (EC 3.5) Acting on carbon-nitrogen bonds, other than peptide bonds; (EC 3.6) Acting on acid anhydrides; (EC 3.7) Acting on carbon-carbon bonds; (EC 3.8) Acting on halide bonds; (EC 3.9) Acting on phosphorus-nitrogen bonds; (EC 3.1) Acting on sulfur-nitrogen bonds; (EC 3.11) Acting on carbon-phosphorus bonds; (EC 3.12) Acting on sulfur-sulfur bonds; (EC 3.13) Acting on carbon-sulfur bonds.

Lyases include those: (EC 4.1) Carbon-carbon lyases; (EC 4.2) Carbon-oxygen lyases; (EC 4.3) Carbon-nitrogen lyases; (EC 4.4) Carbon-sulfur lyases; (EC 4.5) Carbon-halide lyases; (EC 4.6) Phosphorus-oxygen lyases.

Isomerases include those: (EC 5.1) Racemases and epimerases; (EC 5.2) cis-trans-Isomerases; (EC 5.3) Intramolecular isomerases; (EC 5.4) Intramolecular transferases (mutases); (EC 5.5) Intramolecular lyases.

Ligases, include those: (EC 6.1) Forming carbon-oxygen bonds; (EC 6.2) Forming carbon-sulfur bonds; (EC 6.3) Forming carbon-nitrogen bonds; (EC 6.4) Forming carbon-carbon bonds; (EC 6.5) Forming phosphoric ester bonds; (EC 6.6) Forming nitrogen-metal bonds.

Enzymes involved in a pathway may be classified according to the role of the enzymes. Direct involvement enzymes catalyze a reaction in the pathway. It is typical of pathways that such direct enzymes are one of a chain, where a product of a first enzyme is the substrate of a second, etc., which eventually results in the product of interest. Indirect involvement enzymes react in an associated pathway, usually in the production of a substrate used in the pathway. It may be a characteristic of an enzyme in these two classes that overproduction of the enzyme is toxic to the cell, even 2-fold, 3-fold or more overproduction. Such toxicity can be the result of various effects, including overproduction of a product that is toxic at high concentrations, or that the enzyme diverts resources, e.g. an initial substrate, at a rate that impacts the normal cell physiology, etc. The expression of such enzymes benefits from modulated selective increase in expression with the methods of the invention, in order to avoid undesirable stress to the cell.

Within a pathway, enzymes will vary in turnover rate and the effectiveness with which a product is produced. As a result, certain enzymes in a pathway become rate-limiting. Increasing the concentration of rate-limiting enzymes in a pathway (relative to non-rate limiting enzymes) allows increased flux through the pathway of interest. Often rate-limiting enzymes are also associated with toxicity when over-produced, and thus expression of such enzymes is desirably modulated by the methods of the invention to selectively increase expression at a selected time point.

A third class of enzymes are competing enzymes, which utilize a substrate or product of the pathway of interest. A characteristic of a competing enzyme is that the kinetics of the substrate conversion are sufficiently high that the presence of the enzyme decreases the overall yield and/or the rate of production of the desired final product catalyzed by the pathway of interest. A normal cell may require the expression of competing enzymes, and therefore rather than knocking out expression, it is desirable to selectively decrease the concentration of the enzyme by the methods of the invention, e.g. by introducing a site for a sequence-specific protease and inducing protease expression.

For convenience of naming, an enzyme in the pathway may be categorized as a first, pathway entry enzyme, or a subsequent downstream enzyme or enzymes. For convenience, the pathway entry enzyme may be referred to herein as $E_1$, and the downstream enzymes may be consecutively numbered, $E_2$, $E_3$, ... $E_n$. Pathways of interest for the methods of the invention will usually comprise at least two enzymes, and may comprise at least three enzymes, at least four enzymes, or more.

Enzymes in a pathway may be naturally occurring, or modified to optimize a characteristic of interest, e.g. substrate specificity, reaction kinetics, solubility, codon usage, etc. In some embodiments the complete pathway comprises enzymes from a single organism, however such is not required, and combining enzymes from multiple organisms is contemplated. For some purposes a pathway may be endogenous to the host cell, but such is also not required, and a complete pathway or components of a pathway may be introduced into a host cell. Where the system is provided in an intact cell, generally the complete set of enzymes required for pathway conversion will be present in the cell. For purposes of cell-free production, one or more enzymes may be added to the lysate so as to complete the pathway.

In the pathway system, a first substrate ($S_1$) is acted upon by the pathway entry enzyme, and is converted to a first product, although it will be understood by one of skill in the art that an enzyme may act upon more than one substrate simultaneously, and may produce more than one product, such that two or more pathways may be interconnected at a single enzyme. The first product is a substrate ($S_2$) for downstream enzyme $E_2$, and is converted to a second product. Depending on the complexity of the pathway, the second product may be the final product ($P_F$), or may be a substrate ($S_3$) for a third downstream enzyme ($E_3$), and is converted to a third product, which may be a substrate ($S_4$) for a fourth enzyme, etc. The final enzyme in the pathway, which may be $E_2$, $E_3$, $E_4$, etc. produces the product of interest ($P_F$). It is a characteristic of enzyme pathways that the product of one enzyme is the substrate for the next enzyme. Products may be stable or relatively labile, but in general the final product is sufficiently stable that it can be isolated from the cell or reaction mixture.

In some embodiments of the invention, the initial substrate, $S_1$, is a central metabolite, or cellular "commodity". The central pathways of metabolism include glycolysis and the citric acid cycle. Such $S_1$ compounds are generally not specific to the pathway of interest, but are compounds widely found in various cells and are substrates for multiple enzymes and pathways. Examples of commodity substrates include, without limitation, glucose, ATP, pyruvate, phosphoenol pyruvate, and the like. A pathway entry enzyme, $E_1$, may convert a commodity substrate to a product that is a selective substrate for one or a relatively small number of enzymes.

Competing enzymes utilize a substrate or product of the pathway of interest, which may include any one of $P_F$, $S_1$, $S_2$, $S_3$, $S_4$, etc., and may be referred to as competing enzymes ($E_C$).

Figure 2A:
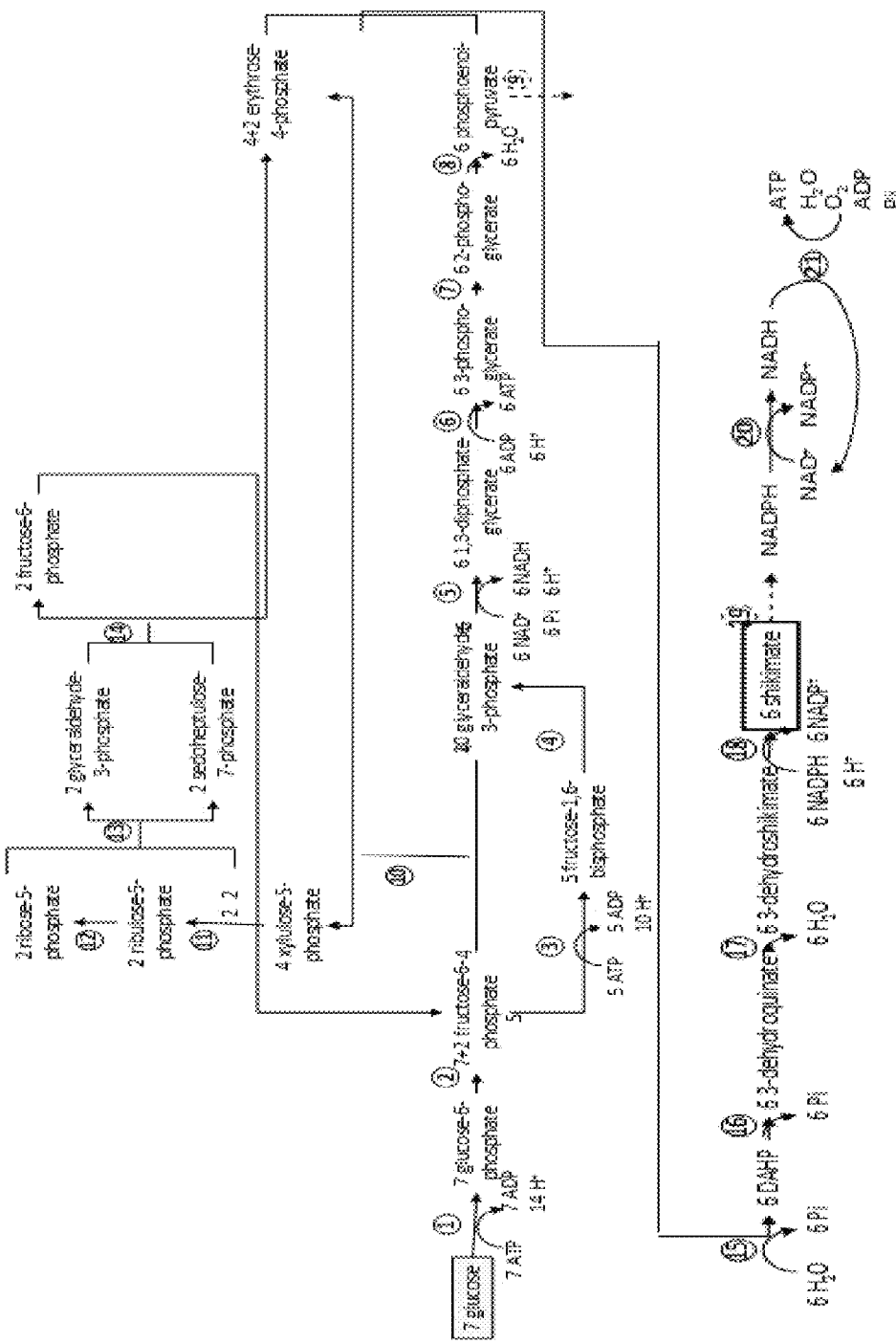

A specific non-limiting example of a pathway is the pathway for the synthesis of shikimic acid. For specific examples of this pathway, see FIG. 1 and FIG. 2. In this pathway, for example, a reaction between the cellular commodity compounds phosphoenolpyruvate ($S_{1A}$) and erythrose-4-phosphate ($S_{1B}$) is catalyzed by the isoenzymes of DAHP synthase, aroFGH ($E_1$) to form 3-deoxy-D-arabino-seheptulose-7-phosphate (DAHP). DAHP ($S_2$) is transformed to 3-dehydroquinate (3-DHQ) by the second enzyme in the pathway, DHQ synthase, aroB ($E_2$). 3-DHQ ($S_3$) is dehydrated to 3-dehydroshikimate by the third enzyme in the pathway, 3-DHQ dehydratase, aroD ($E_3$). 3-dehydroshikimate ($S_4$) is reduced to shikimic acid ($P_F$) by the fourth enzyme in the pathway, shikimate dehydrogenase, aroE ($E_4$), using NADPH as a cofactor. The enzymes of the pathway are known in the art and have been characterized in a number of organisms, including, for example, *E. coli*, in which the enzymes are encoded by the genetic loci as follows: DAHP synthase (aroG, aroF); DHQ synthase (aroB); 3-DHQ dehydratase (aroD); shikimate dehydrogenase (aroE).

In the SA pathway, the overexpression of aroE, aroF, and tktA has been shown to increase the production of SA either directly with aroE and aroF, or indirectly with tktA, which increases the supply of the substrate molecule erythrose-4-phosphate. By protecting the mRNAs of enzymes that are rate-limiting, the pathway flux is increased dramatically.

There are also competing enzymes relevant to this pathway, which utilize the desired final product ($P_F$) as a substrate, which enzymes are shikimate kinase (aroK) and shikimate kinase II (aroL). The presence of active competing enzymes may be undesirable, as they reduce the amount of desired product from the reaction mixture.

Interferase. As used herein, the term interferase refers to a microbial enzyme that is a site specific endoribonuclease (for a review, see Yamaguchi and Inouye (2009) Prog Mol Biol Transl Sci. 85:467-500). Such enzymes may be one of an antitoxin-toxin pair.

In a preferred embodiment the interferase is a sequence specific endoribonuclease. Many such sequence specific endoribonuclease interferase enzymes are known to one of skill in the art, including, without limitation, the *E. coli* enzyme MazF and homologs thereof, which have been shown to be a sequence-specific (ACA) endoribonuclease that cleaves cellular mRNAs and effectively blocks protein synthesis (Zhang et al. (2005) J Biol Chem. 280(5):3143-50). ChpBK is a sequence-specific endoribonuclease that cleaves mRNAs both in vivo and in vitro at the 5'- or 3'-side of the A residue in ACY sequences (Y is U, A, or G) (Zhang et al. (2005) J.B.C. 280:26080-26088). MqsR is a GCU-specific mRNA interferase in *E. coli* (Yamaguchi et al. (2009) J Biol Chem. 284(42):28746-53)

In other embodiments the interferase, or a second interferase used in combination with a sequence specific endoribonuclease, is a site specific endoribonuclease. YafO is a ribosome-dependent mRNA interferase inhibiting protein synthesis (Zhang et al. (2009) J Biol Chem. 284 (38):25522-31. RelE is a site specific endoribonuclease that cleaves mRNA at the A site of a ribosome.

For the purposes of the invention it may be desirable to introduce an exogenous interferase coding sequence into a microbial cell, operably linked to a regulatable promoter, e.g. an inducible promoter, which may be referred to herein as an interferase expression construct. The interfase expression construct may be provided on an episomal vector, e.g. a plasmid, YAC, BAC, viral, etc. vector, as known in the art. Alternatively the interferase expression construct may be integrated into the chromosome of the microbial host cell.

Interferase cleavage site. As described above, a sequence specific interferase enzyme cleaves mRNA in a sequence specific manner, e.g. at GCU, ACA, ACY, etc. The methods of the invention utilize, in part, a modification of targeted genetic sequences to make the sequence of interest interferase resistant. The sequence of interest is altered by one or both of deletion of a residue in the motif for interferase cleavage, or by substitution of a residue in the motif with a neutral residue. By "neutral substitution" it is intended that the nucleotide at a position within the motif is substituted with a nucleotide that maintains the coding sequence or regulatory function, but which alters the sequence such that the motif is no longer present. A transcribed, i.e. mRNA sequence that is devoid of an interferase motif sequence may be referred to as resistant to that interferase.

In some embodiments of the invention, a plurality of pathway enzyme coding sequences are genetically modified to be interferase resistant, usually at least two coding sequences, at least three coding sequences, or more. Such modified coding sequence may be referred to as interferase resistant pathway enzyme sequences. The protected enzymes are usually rate-limiting enzymes in the pathway.

The use of the interferase resistant sequences allows protection of certain mRNAs, usually mRNA encoding rate limiting enzymes, thus increasing flux through a pathway of interest. The mRNAs of the pathway enzymes to be protected do not necessarily have to lie in the shortest path from substrate to product, as long as their overexpression leads to an increase in the flux to product. When the interferase is expressed, the mRNAs that code for most proteins in the cell are cleaved and degraded, but the proteins themselves can stay active for days. The interferase-resistant mRNAs, on the other hand, will not be degraded and the proteins that are coded by them will be overproduced upon activation of the interferase. This, in turn, results in an increased flux through the pathway of interest.

Site specific protease. As used herein, the term refers to a protease, generally an endoprotease, which cleaves selectively at a specific amino acid motif, usually a motif of at least 4 amino acid residues to reduce background protein cleavage, and may be a motif of at least 5 amino acids, at least 6 amino acids, or more. Such proteases are known to those of skill in the art, and include, without limitation, tobacco etch virus protease (ENLYFQ$^G/_S$) (SEQ ID NO 1); yellow fever virus protease (GARR$^G/_S$) (SEQ ID NO 2); thrombin (LVPRGS) (SEQ ID NO 3); Factor Xa (I$^E/_D$GR) (SEQ ID NO 4), etc.

For the purposes of the invention it may be desirable to introduce an exogenous protease coding sequence into a microbial cell, operably linked to a regulatable promoter, e.g. an inducible promoter, which may be referred to herein as an protease expression construct. The promoter may be induced by an agent that is the same or different as the inducing agent for the interferase expression construct, usually different. The protease expression construct may be provided on an episomal vector, e.g. a plasmid, YAC, BAC, viral, etc. vector, as known in the art. Alternatively the protease expression construct may be integrated into the chromosome of the microbial host cell.

In some embodiments, optionally in combination with modification and expression of interferase resistant pathway enzyme sequences, the genetic sequence encoding the protease is modified to be interferase resistant, i.e. lacking any sequence motifs recognized and cleaved by the interferase of interest.

Protease cleavage site. As described above, a sequence specific protease cleave proteins in a sequence specific manner, e.g. at ENLYFQ$^G/_S$ (SEQ ID NO 1), GARR$^G/_S$ SEQ ID N(2), LVPRGS SEQ ID NO 3), I$^E/_D$GR (SEQ ID NO 4), etc. The methods of the invention utilize, in part, a modification of targeted genetic sequences to make a targeted protein labile to protease digestion. In addition, the protease may be selected such that the pathway enzymes of interest are not cleaved by the protease. Alternatively the pathway enzymes of interest are modified such that the proteins are free of protease cleavage motifs.

The protein targeted for protease cleavage is usually a competing enzyme in the pathway of interest, i.e. an enzyme that utilizes a substrate or product of the pathway and by doing so reduces flux through the pathway. The targeted protein is altered by amino acid substitution to generate a cleavage site, preferably by a neutral substitution with conservative amino acid changes. By "neutral substitution" it is intended that the amino acid at a position within the motif is substituted with an amino acid that maintains the enzyme activity. Such an amino acid sequence may be referred to as protease labile sequence. In general the site for cleavage is selected such that, following cleavage, the enzyme activity is destroyed. See Example 2 herein.

"Cell-free system," as used herein, is an isolated cell-free system containing a cell expressly engineered to synthesize an enzyme or cascade of enzymes that, when acting in a given sequence (e.g., in an enzymatic pathway) and proportion over a determined substrate, results in the preferential generation of a compound of interest. A compound of interest is typically a chemical entity (e.g., a small molecule), which can be used as an active pharmaceutical ingredient (API), chemical precursor, or intermediate, etc.

"Substrate," as used herein, is a compound or mixture of compounds capable of providing the required elements needed to synthesize a compound of interest.

"Adenosine triphosphate regeneration system" or "ATP regeneration system," as used herein is a chemical or biochemical system that regenerates AMP and ADP into ATP. Examples of ATP regeneration systems include those involving glucose metabolism, glutamate metabolism, photosynthesis, etc.

"Reducing equivalent," as used herein, is a chemical species which transfers the equivalent of one electron in a redox reaction. Examples of reducing equivalents are a lone electron (for example in reactions involving metal ions), a hydrogen atom (consisting of a proton and an electron), and a hydride ion (:H—) which carries two electrons (for example in reactions involving NAD). A "reducing equivalent acceptor" is a chemical species that accepts the equivalent of one electron in a redox reaction.

Metabolite. A metabolite is any substance produced during metabolism. For the purposes of the present invention, a metabolite is often, although not always, the product of an enzyme in the pathway of interest.

Inducible expression. The methods of the invention make use of regulated expression of various coding sequences, including without limitation the sequences encoding interferase and protease enzymes. Expression may be regulated by various cues, for example induction by chemicals, change of growth phase, depletion of a nutrient, temperature shifts, light, etc. In some embodiments inducible promoters regulated by the presence of an inducing agent, e.g. a chemical such as lactose, arabinose, tetracycline, etc., as known in the art.

Expression and cloning vectors usually contain a promoter that is recognized by the host organism and is operably linked to the coding sequence of interest. Promoters are untranslated sequences located upstream (5') to the start codon of a structural gene that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. While the native promoter may be used, for most purposes heterologous promoters are preferred, as they generally permit greater transcription and higher yields.

Promoters suitable for use with prokaryotic hosts include the β-lactamase and lactose promoter systems, alkaline phosphatase, a tryptophan (trp) promoter system, and numerous hybrid promoters such as the tac promoter. However, other known bacterial promoters are also suitable, e.g. the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Their nucleotide sequences have been published, thereby enabling a skilled worker operably to ligate them to a sequence of interest using linkers or adaptors. Promoters for use in bacterial systems also will contain a Shine-Dalgarno (S.D.) sequence operably linked to the coding sequence.

Promoters suitable for eukaryotic cells, e.g. yeast cells, are also known in the art. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Yeast enhancers also are advantageously used with yeast promoters.

Production Methods

High yield synthesis of a product of interest is accomplished by providing a pathway system comprising pathway enzymes, substrates, co-factors and such salts, buffers, etc. as are required for enzyme activity, in a metabolically frozen cell or lysate thereof. The flux through the pathway and production of the final product is enhanced by genetically engineering the cell to over-produce rate-limiting enzymes in the pathway, and optionally to degrade enzymes that compete for substrates and/or products of the pathway. The cell is metabolically frozen at a desired growth point by inducing expressing of interferase activity, where the pathway enzymes or a subset there, e.g. rate-limiting pathway enzymes, have been modified to be interferase resistant. Modified enzymes may be indirectly related to the pathway of immediate interest if they increase the flux through the pathway. This procedure can be used to overcome regulatory (allosteric, transcriptional, post-transcriptional, etc.) or kinetic limitations. The effect of competing enzymes may be addressed by inducing expression of a sequence specific protease that cleaves one or more of the competing enzymes.

Induction of interferase activity may comprise upregulating expression of the interferase or downregulating expression of the cognate antitoxin for the interferase. The antitoxin may be native or exogenous to the cell, e.g. by expressing a siRNA that targets the antitoxin RNA, by including a protease tag on the antitoxin and express the cognate protease, by a temperature shift that shuts off an antitoxin promoter etc. Upregulation of interferase activity may comprise increasing the copy number of toxin, which would cause its overexpression even if induced from a promoter that is weaker than the native one; introducing mRNA stabilization signals such that the levels of toxin increase with respect to native one when induced; expression of the interferase from an inducible non-native promoter; expression of a non-coding RNA that either stabilizes the toxin, or destabilizes/silences the antitoxin; and the like.

The interferase coding sequence can be under the control of synthetic or native promoters, e.g. to activate the state of interest in response to internal or external signals. Cells can be metabolically frozen in any physiological stage, e.g. after exposure to certain stresses or growth conditions, and in any genotypic background, e.g. endonuclease-resistant sequences of different enzymes can be introduced or chromosomal deletions added, in order to bring about diversion of substrates that are normally used for growth towards pathways or products of interest. Cells of different genetic backgrounds, e.g. previously altered or genetically engineered, or species, or that are prepared by different strategies can be mixed and simultaneously or sequentially used in a bioprocess. The biocatalyst can be free or immobilized, and can be reused or disposed at each stage of the process.

The methods of the invention provide for high yields of the desired product, which yield is greater than the yield that can be achieved with a native microbial host. Productivity (i.e. rate of production per unit of volume or biomass) may also be increased. In one embodiment of the invention, the yield of product is at least about five-fold the basal rate, at least about 10-fold the basal rate, at least about 25-fold the basal rate, or more.

In some embodiments, interferase activity is induced by adding extracellular-death factor (EDF) to the medium, either naturally- or synthetically-derived. Spent medium can also be used to activate the dormant state.

The enzymes being expressed in metabolically-frozen cells can be harmful by themselves or through the enzymatic activities they have, or can be active under unfavorable process conditions, e.g. heat-resistant enzymes, osmotolerant enzymes, engineered enzymes, etc. Gene products that are not needed in the frozen state or that compete with pathways of interest but are essential for growth and thus cannot be deleted completely can be eliminated by modifying the coding sequence to be protease labile.

Different inocula can be adapted to different conditions (e.g. two batches grown on two different carbon sources) or can have different genotypes (e.g. different sets of enzymes made interferase-resistant, different enzymes made protease-labile, etc.) and then mixed to carry out the fermentation (e.g. to get simultaneous consumption of a mix of carbon sources or sequential processing of a metabolite through a pathway divided in two separate batches of cells). Fermentation can also take place sequentially by allowing one set of reactions to proceed in one vessel and then passing the supernatant through a second vessel. The toxin, antitoxin, or enzymes of the pathway of interest (or their mRNAs) can be engineered to manipulate their activity (e.g. by changing the specificity of the endonuclease targets) or otherwise optimized using molecular biology, biochemistry, or similar techniques. The methods can be practiced with intact cells or cell lysates.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

The reactions may be of any volume, either in a small scale, usually at least about 1 ml and not more than about 15 ml, or in a scaled up reaction, where the reaction volume is at least about 15 ml, usually at least about 50 ml, more usually at least about 100 ml, and may be 500 ml, 1000 ml, or greater up to many liters of volume. Reactions may be conducted at any scale.

Various nutrients, salts, and buffers may be included, where ionic and nutrient species are typically optimized with regard to product production. When changing the concentration of a particular component of the reaction medium, that of another component may be changed accordingly. Also, the concentration levels of components in the reactor may be varied over time. The adjuster of oxidation/reduction potential may be dithiothreitol, ascorbic acid, glutathione and/or their oxidized forms.

In a semi-continuous operation mode, the reactor may be operated in dialysis, diafiltration batch or fed-batch mode. A feed solution may be supplied to the reactor through the same membrane or a separate injection unit. Synthesized product is accumulated in the reactor, and then is isolated and purified according to the usual method for purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying transmembrane pressure using other methods known in the art. The solution in contact with the outside surface of the membrane may be cyclically changed, and may be in a steady tangential flow with respect to the membrane. The reactor may be stirred internally or externally by proper agitation means.

The amount of product produced in a reaction can be measured in various fashions. One method relies on the availability of an assay which measures the activity of the particular product being produced.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

EXPERIMENTAL

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

Example 1

Interferase Resistant Pathway Enzymes

The sequences encoding enzymes from shikimic acid pathway enzymes are genetically modified to be interferase resistant by deletion of the ACA motif sequence recognized by mazF interferase. The sequences of *Escherichia coli* feedback-resistant DAHP synthase (encoded by aroG-fbr or aroF-fbr) are obtained (see Ger et al. (1994) J. Biochem. 116, 986-990; Kikuchi et al. (1997) Appl. Environ. Microbiol. 63, 761-762; and Weaver et al. (1990) J. Bacteriol. 172, 6581-6584). The sequence of the wild-type aroF is accessed at Genbank, NP_417092.1. The sequence of wild-type aroG is accessed at Genbank, NP_415275.1. The *E. coli* chromosome sequence is available in Genbank at accession number U00096, and provides the sequence for transketolase (tktA), and shikimate dehydrogenase (aroE).

The sequence corresponding to the mRNA for each of tktA, aroE, and aroG-fbr or aroF-fbr are scanned for the presence of ACA sequences. Each such motif is scored as being present in a coding sequence, a non-coding sequence with regulatory function, and non-coding sequence without regulatory function. For non-coding sequences without regulatory function, one of the nucleotides in the ACA motif is substituted with a different nucleotide. For non-coding sequences with regulatory function, one of the nucleotides can be substituted such that the regulatory function is not altered.

For coding regions, codon degeneracy is used to make changes, such that the amino acid sequence is not changed. Because of degeneracy, this can always be done whenever an A or C falls in the third base of the codon. Since the only amino acids with no degeneracy are methionine and tryptophan, but they do not have A or C in the third base, this does not present a challenge. Whenever more than one choice for codon change is possible, e.g. for arginine, codon usage information of the organism of interest, *E. coli* in this case, is taken into account to decide what substitution to make. After the modified, ACA-less sequence is figured out on paper, the DNA corresponding to the desired sequence is synthesized de nova Alternatively the modifications are done in a cloned version of the gene using standard site-directed mutagenesis protocols, such as those for sale by Stratagene, e.g. Quickchange kit.

The modified sequences are introduced into a host. For initial testing *E. coli* is used as a host, although synthesis of other compounds may utilize other hosts, including, e.g., lactic acid produced in *Lactobacillus* spp. or *Saccharomyces cerevisiae*. The interferase-resistant versions of the genes can be either expressed from their native promoter or, alternatively, from the same inducible promoter from which the interferase is expressed. Preferably the chromosomal copy of the sequence is modified, so that no plasmids or promoter changes are required, although for some purposes a plasmid is used for episomal expression. In that case, the modified pathway enzyme coding sequences can be carried in the same plasmid, in a synthetic operon, or from more than one compatible plasmid, from their native promoters. Multiple compatible plasmids can be introduced into the host microorganism.

Example 2

Protease Labile Competing Enzymes

The sequence encoding the competing enzyme, shikimate kinase I (aroK, Genbank accession number YP_026215.2) is inactivated by the methods set forth in Datsenko and Wanner (2000) Proc Natl Acad Sci USA. 97 (12):6640.

The sequence encoding the competing enzyme, shikimate kinase II (Genbank accession number NP_414922.1) is made susceptible to proteolysis by a site-specific protease, by introducing a protease cleavage site in the target protein through introduction of specific mutations, by recombination, or multiplex genome engineering. The site for protease inactivation is introduced at a suitable site in the enzyme. Alternatively, shikimate kinase II is inactivated by the methods set forth in Datsenko and Wanner (2000), and shikimate kinase I is made susceptible to proteolysis by a site-specific protease.

The sequence of the enzyme is analyzed to identify the amino acid sequence closest to the protease cleavage motif, so that the least number of modifications to the amino acid sequence is needed to get a protease cleavage site. The ideal site is on the surface of the protein, to minimize the effects on enzyme function. A site near the surface also ensures that it is accessible to the protease when folded. Alternatively, an enzyme from a different organism that carries out the same function and contains a protease cleavage site can be used instead of a native enzyme that is not protease labile.

A suitable site for cleavage (a slash indicates alternative amino acids) is the sequence ENLYFQ$^{G}/_S$ (SEQ ID NO 1) (cleaved by the tobacco etch virus protease). An alternative site for cleavage is GARR$^{G}/_S$ (SEQ ID NO 2) (cleaved by the yellow fever virus protease). An alternative site for cleavage is LVPRGS (SEQ ID NO 3) (cleaved by thrombin). An alternative site for cleavage is I$^{E}/_D$GR (SEQ ID NO 4) (cleaved by thrombin). The genetically modified sequence, which may be referred to the protease-labile form of the sequence, is expressed from a plasmid with concomitant inactivation of the chromosomal copy, or used to alter the chromosomal sequence of the host organism. In an alternative embodiment, aroL is inactivated and aroK is made susceptible to proteolysis.

Enzymatic assays are conducted, after a brief scanning of the sequences, to ensure that the chosen protease cleaves the target protein, but not any other protein needed for SA biosynthesis. To accomplish this, the cells modified with the protease-labile competing enzyme are further modified to express the cognate protease under the control of an inducible promoter. The cells are grown in medium containing glucose as a carbon source. The production of shikimic acid in the cells is measured using H-NMR or HPLC, as described by Knop et al. (2001) J. Am. Chem. Soc. 123:

10173-10182 or van Hess et al. (1999) Talanta, 5 Jan. 1999, Pages 173-17], or any other analytical chemistry technique, such as GC-MS.

Alternatively individual enzymatic assays, e.g., in which the depletion of an enzymatic substrate or accumulation of its product is measured in a solution with the purified enzyme protein, is performed.

If any protein in the SA pathway is found to be susceptible to proteolysis, other than the competing enzyme(s), cleavage sites are removed by making conservative amino acid changes by site-directed mutagenesis. Alternatively, an enzyme from a different organism that carries out the same function, but does not contain a protease cleavage site, can be used instead of a native enzyme that is protease labile. Such analysis is repeated if needed until an appropriate protease is found.

Example 3

Interferase Resistant Protease

The genetic sequence encoding the selected site-specific protease is modified to remove ACA sequences by site-directed mutagenesis, as described above in Example 1. The modified sequence is placed under the control of an inducible promoter. In one embodiment the promoter is the Pbad promoter, which is inducible with the inducing agent arabinose. The araE gene, which is responsible for arabinose transport, is optionally placed under a constitutive promoter in the host strain.

Example 4

Inducible Interferase Expression

The genetic sequence encoding the cognate interferase gene for the interferase-resistant pathway enzymes and protease is placed under an inducible promoter. A suitable interferase is mazF. The accession number for *E. coli* mazF is NP_417262.1. The sequence is operably linked to a promoter that is induced with an agent other than the inducer in Example 3. In one embodiment the promoter is the Plac promoter, which is inducible with IPTG. If the promoter leaks, causing the interferase gene to be induced early, extra copies of the repressor, lacI, are introduced into the host cell.

Example 5

Host Cell Growth

Cells incorporating the genetic changes set forth in Examples 1-4 are grown to a desired cell density in liquid medium. At the desired density the inducing agent for the interferase gene is added to the culture at a concentration sufficient to induce expression of the interferase. This induces a state of dormancy with concomitant overproduction of the feedback-resistant DAHP synthase, the transketolase, and the shikimate dehydrogeanse described in Example 1, causing an increased flux through the SA pathway. In this stage, where the pathway enzymes are being overproduced (or later when competing enzymes are cleaved), additional substrates may be required to be added to the medium, including amino acids, vitamins, buffers, etc.

To inactivate competing enzymes, the inducing agent for expression of the protease described in Example 3 is added to the cell culture. Induction of protease expression results in increased proteolysis of the labile shikimate kinase.

Example 6

Host Cell Lysate

The host cells of Example 5 are washed, and resuspended in suitable medium. The cells are lysed by homogenization. Glucose as a substrate for SA production is added to the medium, and synthesis of SA is measured to determine the production of this metabolite in the supernatant, using the assay described in Example 2.

Example 7

For synthesis of SA in intact cells, the host cells of Example 5 are washed and resuspended in suitable medium in the presence of glucose as a substrate.

What is claimed is:

1. A cell lysate of bacterial cells genetically manipulated to comprise:
   (a) a coding sequence for a protease that cleaves proteins at a specific sequence motif that comprises at least 4 amino acid residues, wherein the coding sequence for the protease is operably linked to an inducible promoter; and
   (b) a coding sequence for at least one competing enzyme selected from the group consisting of enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, and glucokinase, wherein the coding sequence for the at least one competing enzyme is modified to encode the specific sequence motif cleaved by the protease.

2. The cell lysate of claim 1, wherein the coding sequence for the protease is present on either an episomal vector or a chromosome.

3. The cell lysate of claim 1, wherein the protease is a tobacco etch virus protease, a yellow fever virus protease, thrombin, or Factor Xa.

4. The cell lysate of claim 1, wherein the specific sequence motif comprises at least 5 amino acid residues.

5. The cell lysate of claim 1, wherein the specific sequence motif comprises at least 6 amino acid residues.

6. The cell lysate of claim 1, wherein the bacterial cell is an *Escherichia coli* cell.

7. The cell lysate of claim 1, further comprising one or more of substrates, nutrients, cofactors, buffers, reducing agents, and ATP generating systems.

8. The cell lysate of claim 1, wherein the at least one competing enzyme is glucose-6-phosphate isomerase.

9. The cell lysate of claim 1, wherein the at least one competing enzyme is glyceraldehyde-3-phosphate dehydrogenase.

10. The cell lysate of claim 1, wherein the at least one competing enzyme is phosphofructokinase.

11. The cell lysate of claim 1, wherein the at least one competing enzyme is 3-phosphoglycerate mutase.

12. The cell lysate of claim 1, wherein the at least one competing enzyme is pyruvate kinase.

13. The cell lysate of claim 1, wherein the at least one competing enzyme is triosephosphate isomerase.

14. The cell lysate of claim 1, wherein the at least one competing enzyme is glucokinase.

* * * * *